US006686180B2

(12) United States Patent
Blake et al.

(10) Patent No.: US 6,686,180 B2
(45) Date of Patent: Feb. 3, 2004

(54) METHOD FOR THE PRODUCTION OF BACTERIAL TOXINS

(75) Inventors: Milan S. Blake, Fulton, MD (US); John A. Bogdan, Jr., Westminster, MD (US); Javier Nazario-Larrieu, Rio Piedras, PR (US)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 0 days.

(21) Appl. No.: 09/825,770

(22) Filed: Apr. 4, 2001

(65) Prior Publication Data

US 2002/0061555 A1 May 23, 2002

Related U.S. Application Data

(60) Provisional application No. 60/194,482, filed on Apr. 4, 2000.

(51) Int. Cl.$^7$ ......................... A01N 63/00; C12P 21/00; C12N 1/38; C12N 1/20

(52) U.S. Cl. ..................... 435/71.3; 435/71.1; 435/244; 435/252.31; 424/93.1; 424/93.46

(58) Field of Search ................................ 424/93.1, 780, 424/93.4, 93.46; 435/69.3, 70.1, 71.1, 71.3, 244, 252.1, 253.6, 252.31

(56) References Cited

U.S. PATENT DOCUMENTS 4,950,599 A 8/1990 Bertling
4,965,205 A * 10/1990 Quentin-Millet et al. ... 435/244
5,272,071 A 12/1993 Chappel
5,338,670 A 8/1994 Sekura et al.
5,460,941 A 10/1995 Camerini-Otero et al.
5,557,032 A 9/1996 Mak
5,612,205 A 3/1997 Kay et al.
5,614,396 A 3/1997 Bradley et al.
5,616,491 A 4/1997 Mak et al.
5,777,195 A 7/1998 Fienberg et al.
5,789,215 A 8/1998 Berns et al.
5,948,653 A 9/1999 Pati et al.
5,965,443 A 10/1999 Reznikoff et al.
6,015,676 A 1/2000 Lin et al.
6,031,149 A 2/2000 Chambon et al.

OTHER PUBLICATIONS

Andresen, L.O., "Studies on the effect of divalent metal ions in exfoliative toxins from *Staphylococcus hycius*:indications of ExhA and ExhB being Metalloproteins," FEMS Immunology and Medical Microbiology, 23:295–301 (1999).*

Frohlich et al., Journal of Biotechnology 39: 205–219 (1995).

* cited by examiner

*Primary Examiner*—James Housel
*Assistant Examiner*—Zachariah Lucas
(74) *Attorney, Agent, or Firm*—Heller Ehrman White & McAuliffe

(57) ABSTRACT

Methods and compositions are provided for the enhanced production of bacterial toxins in large-scale cultures. Specifically, methods and compositions for reducing bacterial toxin expression inhibitors are providing including, but not limited to, addition of toxin expression inhibitor binding compounds, culture media having reduced concentrations of toxin inhibitor metabolic precursors and genetically modified toxogenic bacteria lacking enzymes required to metabolize the toxin inhibitor metabolic precursors.

5 Claims, 16 Drawing Sheets

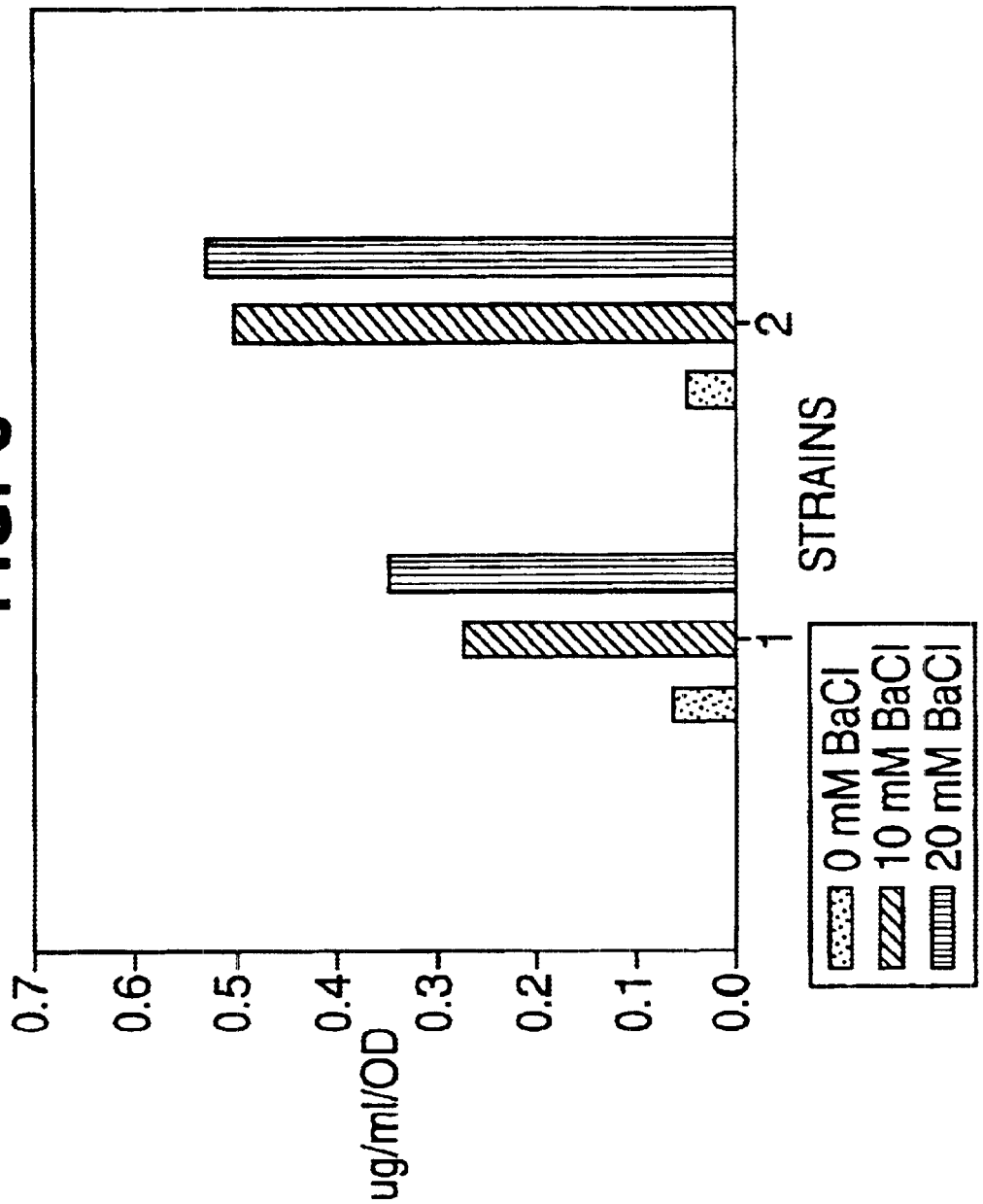

FIG. 7A

```
                       10          20          30          40          50
DSFBP314.AMI    1  MSNRPIYLDY SATTPVDPSV VEKMIPWLYE SFGNPASRSH AFGWEAEDAV   50
DSFBP536.AMI    1  MSNRPIYLDY SATTPVDPSV VEKMIPWLYE SFGNPASRSH AFGWEAEDAV   50
                       60          70          80          90         100
DSFBP314.AMI   51  EKAREEVAKL VNADPREIVW TSGATESDNL AIKGAANFYA ERGKHIITVK  100
DSFBP536.AMI   51  EKAREEVAKL VNADPREIVW TSGATESDNL AIKGAANFYA ERGKHIITVK  100
                      110         120         130         140         150
DSFBP314.AMI  101  TEHKAVLDTC RELERQGFEV TYLDVQDDGL LSLDAFKAAL RPDTILVSVM  150
DSFBP536.AMI  101  TEHKAVLDTC RELERQGFEV TYLDVQDDGL LSLDAFKAAL RPDTILVSVM  150
                      160         170         180         190         200
DSFBP314.AMI  151  MVNNEIGVIQ DIAALGEICR EKGIIFHVDA AQATGKVEID LQKLKVDLMS  200
DSFBP536.AMI  151  MVNNEIGVIQ DIAALGEICR EKGIIFHVDA AQATGKVEID LQKLKVDLMS  200
                      210         220         230         240         250
DSFBP314.AMI  201  FSAHKTYGPK GIGALYVRRK PRVRIEAQMH GGGHERGFRS GTLATHQIVG  250
DSFBP536.AMI  201  FSAHKTYGPK GIGALYVRRK PRVRIEAQMH GGGHERGFRS GTLATHQIVG  250
                      260         270         280         290         300
DSFBP314.AMI  251  MGEAFRLARE EMGTENERVR MLRDRLLAGL TQIEEVYVNG SMEHRVPHNL  300
DSFBP536.AMI  251  MGEAFRLARE EMGTENERVR MLRDRLLAGL TQIEEVYVNG SMEHRVPHNL  300
                      310         320         330         340         350
DSFBP314.AMI  301  NISFNYVEGE SLIMAIKELA VSSGSACTSA SLEPSYVLRA LGRNDELAHS  350
DSFBP536.AMI  301  NISFNYVEGE SLIMAIKELA VSSGSACTSA SLEPSYVLRA LGRNDELAHS  350
                      360         370         380         390         400
DSFBP314.AMI  351  SIRFTLGRFT TEQEIDFTIE LIKSRVGKLR DMSPLWEMAQ EGIDLNSVQM  400
DSFBP536.AMI  351  SIRFTLGRFT TEQEIDFTIE LIKSRVGKLR DMSPLWEMAQ EGIDLNSVQM  400
                      410         420         430         440         450
DSFBP314.AMI  401  AAH*......  ..........  ..........  ..........  ..........  450
DSFBP536.AMI  401  AAH*......  ..........  ..........  ..........  ..........  450
                       10          20          30          40          50
DSF314.DNA      1  ATGAGCAATC GCCCCATCTA CCTGGACTAC TCGGCTACCA CGCCGGTCGA   50
DSF536F1.DNA    1  ATGAGCAATC GCCCCATCTA CCTGGACTAC TCGGCTACCA CGCCGGTCGA   50
DSF536R1.DNA    1  ..........  ..........  ..........  ..........  ..........   50
DSF53611.DNA    1  ..........  ..........  ..........  ..........  ..........   50
DSF53612.DNA    1  ..........  ..........  ..........  ..........  ..........   50
```

FIG. 7B

|  |  | 60 | 70 | 80 | 90 | 100 |  |
|---|---|---|---|---|---|---|---|
| DSF314.DNA | 51 | CCCGAGCGTG | GTCGAGAAAA | TGATTCCCTG | GTTGTACGAG | AGTTTCGGCA | 100 |
| DSF536F1.DNA | 51 | CCCGAGCGTG | GTCGAGAAAA | TGATTCCCTG | GTTGTACGAG | AGTTTCGGCA | 100 |
| DSF536R1.DNA | 51 | .......... | .......... | .......... | .......... | .......... | 100 |
| DSF53611.DNA | 51 | .......... | .......... | .......... | .......... | .......... | 100 |
| DSF53612.DNA | 51 | .......... | .......... | .......... | .......... | .......... | 100 |
|  |  | 110 | 120 | 130 | 140 | 150 |  |
| DSF314.DNA | 101 | ATCCGGCCTC | GCGCAGCCAC | GCCTTTGGCT | GGGAAGCCGA | GGACGCGGTC | 150 |
| DSF536F1.DNA | 101 | ATCCGGCCTC | GCGCAGCCAC | GCCTTTGGCT | GGGAAGCCGA | GGACGCGGTC | 150 |
| DSF536R1.DNA | 101 | .......... | .......... | .......... | .......... | .......... | 150 |
| DSF53611.DNA | 101 | .......... | .......... | .......... | .......... | .......... | 150 |
| DSF53612.DNA | 101 | .......... | .......... | .......... | .......... | .......... | 150 |
|  |  | 160 | 170 | 180 | 190 | 200 |  |
| DSF314.DNA | 151 | GAGAAGGCCC | GCGAGGAAGT | TGCCAAGCTG | GTCAACGCCG | ATCCGCGCGA | 200 |
| DSF536F1.DNA | 151 | GAGAAGGCCC | GCGAGGAAGT | TGCCAAGCTG | GTCAACGCCG | ATCCGCGCGA | 200 |
| DSF536R1.DNA | 151 | .......... | .......... | .......... | .......... | .......... | 200 |
| DSF53611.DNA | 151 | .......... | .......... | .......... | .......... | .......... | 200 |
| DSF53612.DNA | 151 | .......... | .......... | .......... | .......... | .......... | 200 |
|  |  | 210 | 220 | 230 | 240 | 250 |  |
| DSF314.DNA | 201 | GATCGTCTGG | ACTTCCGGCG | CTACCGAGTC | GGACAACCTG | GCCATCAAGG | 250 |
| DSF536F1.DNA | 201 | GATCGTCTGG | ACTTCCGGCG | CTACCGAGTC | GGACAACCTG | GCCATCAAGG | 250 |
| DSF536R1.DNA | 201 | .......... | .......... | .......... | .......... | .......... | 250 |
| DSF53611.DNA | 201 | .......... | .......... | .......... | .......... | .......... | 250 |
| DSF53612.DNA | 201 | .......... | .......... | .......... | .......... | .......... | 250 |
|  |  | 260 | 270 | 280 | 290 | 300 |  |
| DSF314.DNA | 251 | GCGCGGCGAA | TTTCTACGCC | GAGCGCGGCA | AGCACATCAT | TACCGTCAAG | 300 |
| DSF536F1.DNA | 251 | GCGCGGCGAA | TTTCTACGCC | GAGCGCGGCA | AGCACATCAT | TACCGTCAAG | 300 |
| DSF536R1.DNA | 251 | .......... | .......... | .......... | .......... | .......... | 300 |
| DSF53611.DNA | 251 | .......... | .......... | .......... | .......... | .......... | 300 |

FIG. 7C

```
                         310        320        330        340        350
DSF314.DNA     301 ACCGAACACA AGGCGGTGCT GGATACCTGT CGGGAGCTCG AACGCCAGGG  350
DSF536F1.DNA   301 ACCGAACACA AGGCGGTGCT GGATACCTGT CGGGAGCTCG AACGCCAGGG  350
DSF536R1.DNA   301 .......... .......... .......... .......... ..........  350
DSFS3611.DNA   301 .......... .......... .......... .......... ..........  350
DSFS3612.DNA   301 .......... .......... .......... .......... ..........  350
                         360        370        380        390        400
DSF314.DNA     351 CTTTGAAGTG ACCTACCTGG ATGTCCAGGA CGATGGTCTG CTCAGCCTCG  400
DSF536F1.DNA   351 CTTTGAAGTG ACCTACCTGG ATGTCCAGGA CGATGGTCTG CTCAGCCTCG  400
DSF536R1.DNA   351 .......... .......... .......... .......... ..........  400
DSFS3611.DNA   351 .......... .......... .......... .......... ..........  400
DSFS3612.DNA   351 .......... .......... .......... .......... ..........  400
                         410        420        430        440        450
DSF314.DNA     401 ATGCGTTCAA GGCTGCGCTG CGCCCGGATA CCATCCTGGT GTCGGTGATG  450
DSF536F1.DNA   401 ATGCGTTCAA GGCTGCGCTG CGCCCGGATA CCATCCTGGT GTCGGTGATG  450
DSF536R1.DNA   401 .......... .......... .......... .......... ..........  450
DSFS3611.DNA   401 .......... .......... .......... .......... ..........  450
DSFS3612.DNA   401 .......... .......... .......... ----CCTGGT GTCGGTGATG  450
                         460        470        480        490        500
DSF314.DNA     451 ATGGTCAACA ACGAGATCGG CGTCATCCAG GACATCGCCG CGCTGGGCGA  500
DSF536F1.DNA   451 ATGGTCAACA ACGAGATCGG CGTCATCCAG GACATCGCCG CGCTGGGCGA  500
DSF536R1.DNA   451 .......... .......... .......... .......... ..........  500
DSFS3611.DNA   451 .......... .......... .......... .......... ..........  500
DSFS3612.DNA   451 ATGGTCAACA ACGAGATCGG CGTCATCCAG GACATCGCCG CGCTGGGCGA  500
                         510        520        530        540        550
DSF314.DNA     501 GATCTGCCGC GAGAAGGGCA TCATCTTCCA CGTGGACGCG GCCCAGGCCA  550
DSF536F1.DNA   501 GATCTGCCGC GAGAAGGGCA -CATCTTCCA CGTGGACGCG GCC-AAGCCA  550
DSF536R1.DNA   501 .......... .......... .......... .......... ..........  550
DSFS3611.DNA   501 .......... .......... .......... .......... .........C  550
DSFS3612.DNA   501 GATCTGCCGC GAGAAGGGCA TCATCTTCCA CGTGGACGCG GCCCAGGCCA  550
```

FIG. 7D

```
                       560        570        580        590        600
DSF314.DNA     551 CCGGCAAGGT CGAGATCGAC CTGCAGAAGC TGAAGGTGGA CCTGATGTCG    600
DSF536F1.DNA   551 ACGGCAAGGT CGAGATC---  ---------- ---------- ----------    600
DSF536R1.DNA   551 ---------- ---------- ---------- ---------- ----------    600
DSF53611.DNA   551 ---------- -----TCGAC CTGCAGAAGC TGAAGGTGGA CCTGATGTCG    600
DSF53612.DNA   551 CCGGCAAGGT CGAGATCGAC CTGCAGAAGC TGAAGGTGGA CCTGATGTCG    600

610        620        630        640        650
DSF314.DNA     601 TTCTCGGCGC ACAAGACGTA CGGCCCCAAG GGCATCGGCG CGCTGTATGT    650
DSF536F1.DNA   601 ---------- ---------- ---------- ---------- ----------    650
DSF536R1.DNA   601 ---------- ---------- ---------- ---------- ----------    650
DSF53611.DNA   601 TTCTCGGCGC ACAAGACGTA CGGCCCCAAG GGCATCGGCG CGCTGTATGT    650
DSF53612.DNA   601 TTCTCGGCGC ACAAGACGTA CGGCCCCAAG GGCATCGGCG CGCTGTATGT    650

660        670        680        690        700
DSF314.DNA     651 GCGGCGCAAG CCGCGCGTGC GCATCGAGGC GCAGATGCAC GGCGGCGGCC    700
DSF536F1.DNA   651 ---------- ---------- ---------- ---------- ----------    700
DSF536R1.DNA   651 --GGCGCAAG CCGCGCGTGN GNATCGAGGC GCAGATGCAC GGCGGCGGCC    700
DSF53611.DNA   651 GCGGCGCAAG CCGCGCGTGC GCATCGAGGC GCAGATGCAC GGCGGCGGCC    700
DSF53612.DNA   651 GCGGCGCAAG CCGCGCGTGC GCATCGAGGC NTAGATGCAC GGCGGCGGCC    700

710        720        730        740        750
DSF314.DNA     701 ACGAACGGGG CTTCCGGTCG GCCACGCTGG CCACGCACCA GATCGTCGGC    750
DSF536F1.DNA   701 ---------- ---------- ---------- ---------- ----------    750
DSF536R1.DNA   701 ACGAACGGGG CTTCCGGTCG GCCACGNTGG CCACGCACCA GATCGTCGGC    750
DSF53611.DNA   701 ACGAACGGGG CTTCCGGTCG GCCACGCTGG CCACGCACCA GATCGTCGGC    750
DSF53612.DNA   701 ACGAACG--- ---------- ---------- ---------- ----------    750

760        770        780        790        800
DSF314.DNA     751 ATGGGCGAGG CGTTCCGCCT GGCGCGCGAG GAAATGGGCA CCGAGAACGA    800
DSF536F1.DNA   751 ---------- ---------- ---------- ---------- ----------    800
DSF536R1.DNA   751 ATGGGCGAGG CGTTCCGCCT GGCGCGCGAG GAAATGGGCA CCGAGAACGA    800
DSF53611.DNA   751 ATGGGCGAGG CGTTCCGCCT GGCGCGCGAG GAAATGGGCA CCGAGAACGA    800
DSF53612.DNA   751 ---------- ---------- ---------- ---------- ----------    800

810        820        830        840        850
DSF314.DNA     801 GCGCGTGCGC ATGCTGCGCG ACCGCCTGCT GGCCGGCCTG ACGCAGATCG    850
DSF536F1.DNA   801 ---------- ---------- ---------- ---------- ----------    850
DSF536R1.DNA   801 GCGCGTGCGC ATGCTGCGCG ACCGCCTGCT GGCCGGCCTG ACGCAGATCG    850
DSF53611.DNA   801 GCGCGTGCGC ATGCTGCGCG ACCGCCTGCT GGCCGGCCTG ACGCAGATCG    850
DSF53612.DNA   801 ---------- ---------- ---------- ---------- ----------    850
```

FIG. 7E

```
                       860        870        880        890        900
DSF314.DNA    851 AGGAAGTGTA TGTGAACGGC AGCATGGAGC ACCGCGTGCC GCACAACCTG   900
DSF536F1.DNA  851 .......... .......... .......... .......... ..........   900
DSF536R1.DNA  851 AGGAAGTGTA TGTGAACGGC AGCATGGAGC ACCGCGTGCC GCACAACCTG   900
DSF53611.DNA  851 AGGAAGTGTA TGTGAACGGC AGCATGGAGC ACCGCGTGCC GCACAACCTG   900
DSF53612.DNA  851 .......... .......... .......... .......... ..........   900

910        920        930        940        950
DSF314.DNA    901 AACATCAGCT TCAACTATGT CGAGGGCGAG TCTCTGATCA TGGCGATCAA   950
DSF536F1.DNA  901 .......... .......... .......... .......... ..........   950
DSF536R1.DNA  901 AACATCAGCT TCAACTATGT CGAGGGCGAG TCTCTGATCA TGGCGATCAA   950
DSF53611.DNA  901 AACATCAGCT TCAACTATGT CGAGGGCGAG TCTCTGATCA TGGCGATCAA   950
DSF53612.DNA  901 .......... .......... .......... .......... ..........   950

960        970        980        990       1000
DSF314.DNA    951 GGAGCTGGCC GTTCCAGCG GTTCGGCCTG CACGTCGGCC AGCCTGGAGC   1000
DSF536F1.DNA  951 .......... .......... .......... .......... ..........   1000
DSF536R1.DNA  951 GGAGCTGGCC GTTCCAGCG GTTCGGCCTG CACGTCGGCN AGCCTGGAGC   1000
DSF53611.DNA  951 GGAGCTGGCC GTTCCAGCG GTTCGGCCTG CACGTCGGC- ..........   1000
DSF53612.DNA  951 .......... .......... .......... .......... ..........   1000

1010       1020       1030       1040       1050
DSF314.DNA   1001 CGTCCTATGT GCTGCGCGCG CTGGGCCGCA ACGACGAGCT GGCGCACAGC   1050
DSF536F1.DNA 1001 .......... .......... .......... .......... ..........   1050
DSF536R1.DNA 1001 CGTCCTATGT GCTGCGCGCG CTGGGCCGCA ACGACGAGCT GGCGCACAGC   1050
DSF53611.DNA 1001 .......... .......... .......... .......... ..........   1050
DSF53612.DNA 1001 .......... .......... .......... .......... ..........   1050
```

FIG. 7F

```
                     1060       1070       1080       1090       1100
DSF314.DNA      1051 TCCATCCGCT TTACCCTGGG CCGCTTCACG ACCGAACAGG AAATCGACTT 1100
DSF536F1.DNA    1051 .......... .......... .......... .......... ..........  1100
DSF536R1.DNA    1051 TCCATCCGCT TTACCCTGGG CCGCTTCACG ACCGAACAGG AAATCGACTT 1100
DSF53611.DNA    1051 .......... .......... .......... .......... ..........  1100
DSF53612.DNA    1051 .......... .......... .......... .......... ..........  1100

1110       1120       1130       1140       1150
DSF314.DNA      1101 CACGATCGAA CTGATCAAGA GTCGTGTCGG CAAGCTGCGC GATATGTCGC 1150
DSF536F1.DNA    1101 .......... .......... .......... .......... ..........  1150
DSF536R1.DNA    1101 CACGATCGAA CTGATCAAGA GTCGTGTCGG CAAGCTGCGC GATATGTCGC 1150
DSF53611.DNA    1101 .......... .......... .......... .......... ..........  1150
DSF53612.DNA    1101 .......... .......... .......... .......... ..........  1150

1160       1170       1180       1190       1200
DSF314.DNA      1151 CGTTGTGGGA AATGGCCCAG GAAGGCATTG ATCTGAATTC CGTGCAGTGG 1200
DSF536F1.DNA    1151 .......... .......... .......... .......... ..........  1200
DSF536R1.DNA    1151 CGTTGTGGGA AATGGCCCAG GAAGGCATTG ATCTGAATTC CGTGCAGTGG 1200
DSF53611.DNA    1151 .......... .......... .......... .......... ..........  1200
DSF53612.DNA    1151 .......... .......... .......... .......... ..........  1200

1210       1220       1230       1240       1250
DSF314.DNA      1201 GCCGCGCACT GA........ .......... .......... ..........  1250
DSF536F1.DNA    1201 .......... ..                                            1250
DSF536R1.DNA    1201 GCCGCGCACT GA........ .......... .......... ..........  1250
DSF53611.DNA    1201 .......... ..                                            1250
DSF53612.DNA    1201 .......... .                                             1250
```

US 6,686,180 B2

METHOD FOR THE PRODUCTION OF BACTERIAL TOXINS

CROSS REFERENCE TO RELATED APPLICATIONS

This application claims priority to U. S. Provisional Application No. 60/194,482, filed Apr. 4, 2000, which application is incorporated by reference in its entirety.

REFERENCE TO SEQUENCE LISTING, TABLES OR COMPUTER PROGRAM LISTING

A Sequence Listing in computer readable format is included herewith.

BACKGROUND OF THE INVENTION

The present invention relates to increasing bacterial toxin production using methods and compositions that reduce, or eliminate, the accumulation of intracellular and extracellular toxin expression inhibitors. Specifically, the present invention related to methods and compositions for reducing or elimination the accumulation of Bordetella species toxin expression inhibitors. More specifically, the present invention relates to the high yield production of pertussis toxin, pertactin, adenylate cyclase toxin-hemolysin, filamentous hemagglutinin and other toxins.

Pertussis toxin (PT) is one of the various components produced by virulent *B. pertussis*, the microorganism that causes whooping cough. Whooping cough is a serious infection of the respiratory system that at one time was responsible for the death of 5,000 to 10,000 people in the United States each year. Since the advent of the whooping cough vaccine the number of whooping cough related deaths has been reduced to less than 20 annually. Currently, about 50% of all whooping cough infections occur in children less than 1 year old, and only 15% occur in children over than 15 years old. Kids Health.org (visited Mar. 23, 2000) <http://kidshealth.org/parent/common/whooping_cough.html>.

PT is a major protective antigen in the vaccine against whooping cough. Other components of interest produced by *B. pertussis* are filamentous hemagglutinin, heat labile toxin, adenylate cyclase and the like, which may also play important role as protective antigens. Large-scale production of these components, which are useful as diagnostic or chemical reagents and in the preparation of vaccines, requires large-scale cultivation of the microorganism. However, *B. pertussis* is a fastidious organism that has proved difficult to grow in large fermentors. Older methods for the culture of *B. pertussis* employ cultivation in stationary culture or in fermentors. Growth in a stationary culture is labor intensive, while cultivation on a fermentation scale requires vortex stirring and surface aeration. As a result, the effective volume of the fermentor is reduced and modification of the fermentor for growth of pertussis is often necessary. Furthermore, the quantities of PT produced during fermentation under these conditions are variable and often low.

U.S. Pat. No. 5,338,670 discloses a method for the production of *B. pertussis* in the presence of an iron salt, namely ferrous sulfate. While high iron content supports greater bacterial growth, it suppresses the production of PT. By adjusting the iron content of modified Stainer-Scholte media to 10% of the recommended concentration, the production of PT was optimized.

The present invention seeks to improve the yield of PT obtained from *B. Pertussis* by (1) introducing a soluble salt into the growth medium that sequesters sulfate ($SO_4^{2-}$) and/or (2) employing a *B. Pertussis* cysteine desulfinase knockout mutant.

BRIEF SUMMARY OF THE INVENTION

The present invention is based upon the discovery that bacterial toxin expression inhibitors accumulate in culture media and thus significantly reduce toxin production. Moreover, the present invention is based on the findings that suppressing or eliminating toxin expression inhibitors can significantly up regulate toxin expression. Non-limiting examples of the present invention are disclosed using Bordetella sp., specifically, *B. Pertussis* and/or *B. bronchiseptica* which produce pertussis toxin (PT) and pertactin respectively. However, it is understood, that higher bacterial toxin levels can be achieved in other bacterial culture systems using the teachings of the present invention including but not limited to adenylate cyclase toxin-hemolysin, and filamentous hemagglutinin.

Generally, the present invention is exemplified by disclosing methods and compositions used to cultivate *B. Pertussis* that eliminate, or reduce, intracellular and extracellular PT inhibitor accumulation resulting in significant PT production increases.

In one embodiment of the present invention methods and compositions for preparing novel culture media that support *B. Pertussis* growth and prevent or decrease PT inhibition expression by sulfate anions are disclosed. These media compositions and related methods include, but are not limited to, admixing a *B. Pertussis* culture medium with an effective amount of one or more soluble metal salts that form substantially insoluble complexes with sulfate anions.

In another embodiment of the present invention culture media that support *B. pertussis* growth comprising an amount of one or more soluble salts that form substantially insoluble complexes with PT inhibitors, wherein said amount prevents or reduces the inhibition of PT expression are provided. Specifically, soluble metal salts are disclosed that form substantially insoluble complexes with sulfate anions.

Other embodiments of the present invention include *B. Pertussis* culture media and methods for making and using same that reduce PT inhibitors by limiting or eliminating media constituents that contribute to PT inhibitor accumulation. Specifically, in one embodiment of the present invention cysteine concentration is reduced.

The invention also relates to methods and compositions for producing PT comprising cultivating *B. Pertussis* under conditions that eliminate, or reduce, the accumulation of PT inhibitors in the culture media resulting in significant PT production increases and isolating the PT from the culture medium.

In yet another embodiment of the present invention PT production is enhanced using *B. Pertussis* cysteine desulfinase knockout mutants. In one embodiment of the present invention methods of producing PT comprising growing a *B. Pertussis* cysteine desulfinase knockout mutant in a *B. Pertussis* culture medium, and isolating the PT from the culture medium are provided.

BRIEF DESCRIPTION OF THE DRAWINGS

FIG. 6: Graph demonstrating the effect of increasing concentrations of $BaCl_2$ (mM) on the amount of PT produced ($\mu$g/ml/$OD_{650}$) for two B. Pertussis strains (strain 1=CS-87, strain 2=ATCC 9797).

FIG. 7a, FIG. 7b, FIG. 7c, FIG. 7d, FIG. 7e and FIG. 7f: Depict a comparison of the DNA sequence and translated amino acid sequnce of the cysteine desulfinase gene isolated from B. Pertussis strain BP536 with the B. Pertussis sequence (contig 314) found in The Sanger Centre DNA data base.

DETAILED DESCRIPTION OF THE INVENTION

Figure 1:
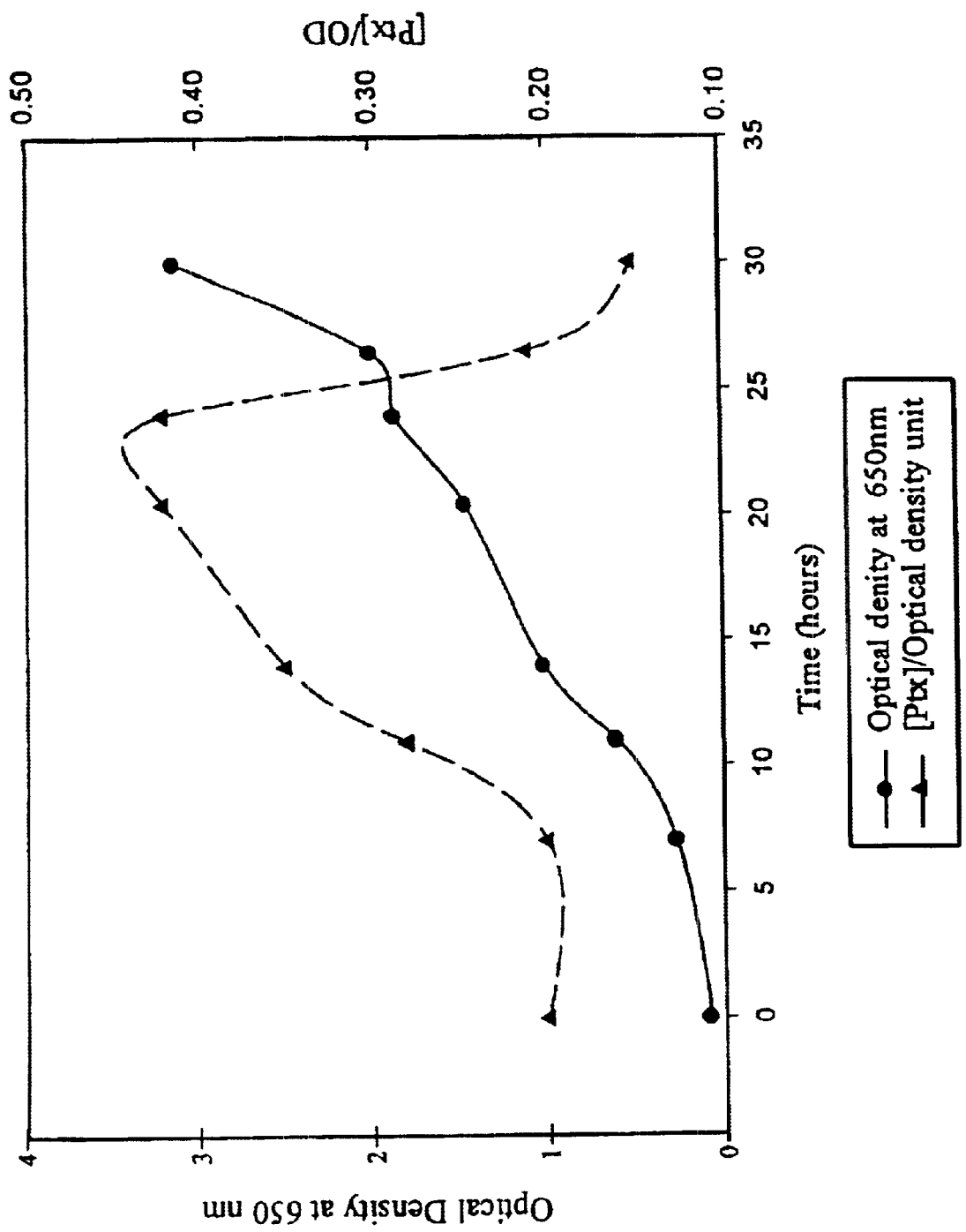
FIG. 1: Graph showing the growth of *B. Pertussis* (OD 650) as well as changes in the amounts of PT ([Ptx]/OD) produced as a function of fermentation time.
Figure 2:
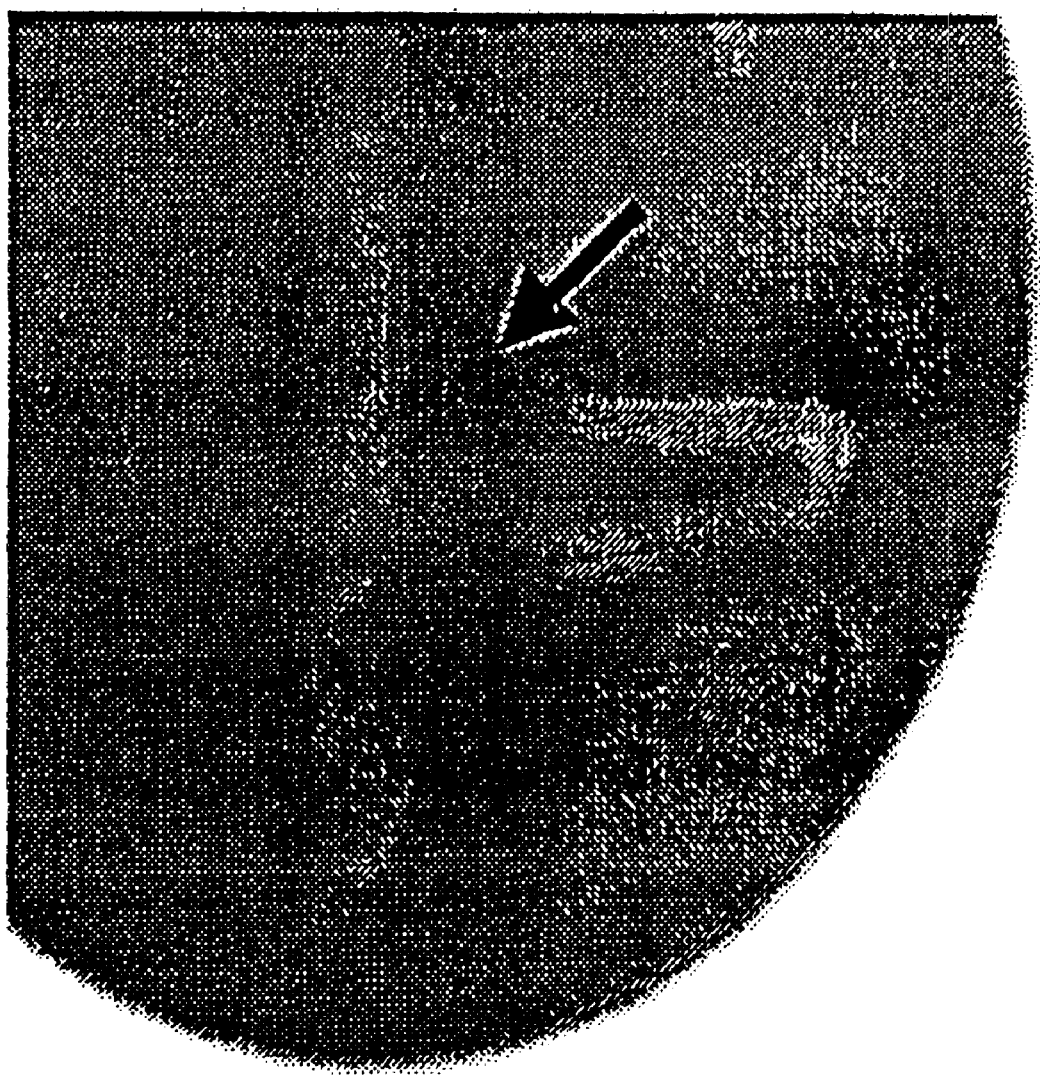
FIG. 2: Picture of a blood agar plate.
Figure 3:
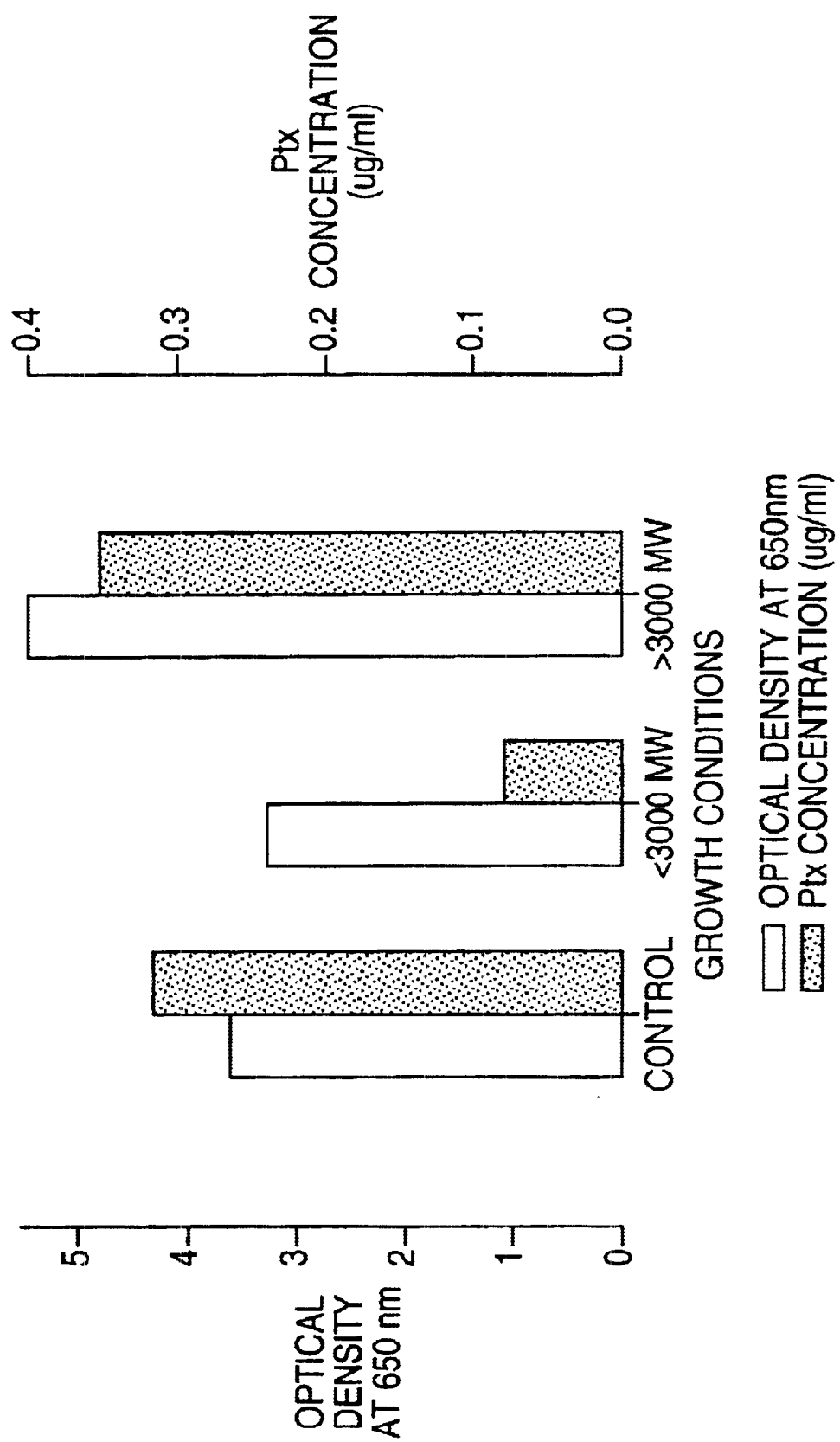
FIG. 3: Bar graph showing growth of *B. Pertussis* (OD 650) and amount of PT (Ptx Conc.) in control culture supernatant (Ctr.), culture medium containing molecules <3,000 KDa (<3K) from spent culture media, and culture medium containing molecules >3,000 KDa (>3K) from spent culture media.

The most serious consequences of bacterial infections often result from toxin expression in the host. Non-limiting examples include, Clostridium tetani which produces tetanus toxin, neurotoxins produced by C. botulinum, C. difficile which produces toxins that cause pseudomembranous colitis, Salmonella typhi produces enterotoxins that cause gastroenteritis and typhoid fever, Staphylococcus aureus can express toxins that cause septic shock and B. Pertussis produces toxins responsible for whooping cough. Other toxogenic genera of bacteria include, but are not limited to, Escherichia, Shigella, and Vibrio. Fortunately, vaccines are available that prevent and/or palliate the most severe effects of bacterial toxins. These vaccines are primarily composed of modified bacterial toxins, sub-lethal doses of purified toxin and or/or whole cell homogenates.

Bordetella pertussis vaccines have proven particularly effective in preventing whooping cough in vaccine recipients. Acellular pertussis (AP) vaccines containing Pertussis toxin (PT) alone or in combination with other antigens of B. Pertussis have been found to be very effective in the prevention of pertussis infections. However, because PT and many of the other pertussis antigens are expressed in minute quantities, it is important to optimize culture conditions to maximize yields. Using the standard Stainer-Scholte (SS) media, a reduction in the pertussis toxin/optical density (PT/$OD_{650}$) ratio midway through batch fermentations was observed. To determine whether this phenomenon was due to a lack of substrate availability or negative feedback inhibition, studies were conducted to determine whether spent media contained inhibitory factors for PT expression and to identify these factors. Culture supernatant samples were take from various stages of fermentation and re-supplied with SS media components lacking the basic salts. These samples were used to initiate a second culture and PT/$OD_{650}$ ratios measured as compared to fresh SS media. Both intact spent media and a fraction of this media containing molecules <3,000 kDa inhibited the production of PT. Cross-streaking experiments on Bordet-Gengou Agar (BGA) confirmed the production of inhibitor(s) of hemolytic activity in freshly streaked bacteria. Coomassie stained gels showed that the whole cell protein profiles were significantly different in the fraction media compared to fresh media suggesting that the inhibitory factors were influencing the two component regulatory system. To further identify these inhibitory compound(s), a complete flux analysis of the intermediate metabolism of B. Pertussis was performed including amino acid and organic acid analysis by HPLC of the spent media as well as crucial enzymes within these pathways. The sulfur-containing amino acid, methionine, and pyruvate, were found to accumulate during late exponential phase of growth (up to 200 mg/L). Examination of all supernatant fractions by LC-MS suggests that pathways for cysteine consumption lead to the formation of sulfate. This in turn acted as a negative feedback inhibitor of PT expression.

Since sulfate acts as an inhibitor of PT expression in B. Pertussis, methods were developed for reducing or eliminating intracellular and extracellular sulfate accumulation as the fermentation proceeds. In one embodiment of the present invention these methods include the addition of an effective amount of a soluble salt that forms a substantially insoluble complex with sulfate. Such soluble salts include alkali earth metal salts or other salts of Pb and Ag. Preferred salts of the present invention are alkali earth metal salts. More preferred salts are Ba(II) halide salts. The most preferred Ba(II) halide salt is $BaCl_2$ or $BaBr_2$.

Barium chloride has been shown to be effective in promoting an increase in the amount of PT produced by B. Pertussis. A ten-fold increase per OD unit in the yield of PT was observed when the ATCC 9797 or CS87 B. Pertussis strain was cultivated in the presence of $BaCl_2$. In this case, the amount of PT in the absence of $BaCl_2$ was 0.05 $\mu$g/mL/$OD_{650}$ as compared to 0.525 $\mu$g/mL/$OD_{650}$ with 20 mM $BaCl_2$. By "effective amount" of a salt is meant an amount that prevents or reduces inhibition of PT expression by sulfate during fermentation compared to when the fermentation is performed in the absence of the salt.

The solubility of the sulfate complex is defined by the solubility product ($K_{sp}$). The sulfate complex is defined as "substantially insoluble" when the lip is approximately $1 \times 10^{-5}$ or less at 25° C. Preferably, the $K_{sp}$ is from about $1 \times 10^{-7}$ to about $1 \times 10^{-10}$ at 25° C. Most preferably the $K_{sp}$ is from about $1 \times 10^{-8}$ to about $1 \times 10^{-10}$ at 25° C. Solubility products that fall within the aforementioned ranges for selected sulfate complexes are shown in Table 1.

TABLE 1

| $K_{sp}$ Values for Selected Sulfate Complexes | |
|---|---|
| Complex | $K_{sp}$ (at 25° C.)[a] |
| $BaSO_4$ | $1.05 \times 10^{-10}$ |
| $PbSO_4$ | $1.82 \times 10^{-8}$ |
| $SrSO_4$ | $3.42 \times 10^{-7}$ |
| $AgSO_4$ | $1.19 \times 10^{-5}$ |

[a]CRC Handbook of Chemistry and Physics-65th Ed., Weast (ed.), p. B-220 (1984).

The sulfate complexes shown in Table 1 are meant to be examples and, as such, are not meant to narrow the scope of the present invention. In addition, it should be noted that the sulfate complex need not be completely insoluble in the growth medium. The sulfate complex must simply be sufficiently insoluble to prevent or reduce inhibition of PT expression by sulfate.

The salts of the present invention may be added to the medium before or after the cultivation of B. Pertussis is initiated. Alternatively, the salt may be admixed with the other components of the medium prior to or after the addition of the water used in the preparation of the medium, but before the introduction of the B. Pertussis cells.

An amount of the salt that may be used in the present invention to promote an increase in the amount of PT produced during fermentation may be from about 0.05 mM to about 50 mM, more preferably, from about 10 mM to about 30 mM, most preferably, about 20 mM. Normally from about 10 mM to about 20 mM of the salt is effective to prevent or reduce inhibition of PT expression by sulfate. One of ordinary skill in the art can determine the optimal amount of salt that effectively prevents or reduces inhibition of PT expression in any particular B. Pertussis strain with no more than routine experimentation.

In another embodiment the present inventors have determined that regulating media concentrations of toxin inhibitor precursors can reduce both intracellular and extracellular toxin inhibitor concentrations. For example, and not intended as a limitation, the present inventors have determined that the PT inhibitors including, but not limited to, sulfites and sulfates are produced as end products of cysteine metabolism. Briefly, Bordetella metabolizes the sulfur containing amino acid cysteine via a pathway involving the enzyme cysteine desulfinase. During cysteine metabolism, a sulfhyral group is enzymatically cleaved from the cysteine molecule. This sulfhyral group is further metabolized into sulfites and sulfates that accumulate within the bacterial cell and the extracellular milieu. Consequently, the longer Bordetella is grown in the presence of cysteine, the higher the intracellular and extracellular sulfate concentrations become and the less PT produced.

Based on the relationship between initial culture media cysteine concentrations and final sulfate concentrations, the present inventors developed the non-limiting theory that reducing the initial cysteine concentrations would result in reduced intracellular and extracellular sulfate accumulation and consequently, reduced PT inhibition. To evaluate the effect that varying cysteine concentrations have on sulfate concentration, the present inventors developed a three different culture systems identified using the following abbreviations: LCMSSB, LCMSSFB and LCMSSBa. The LCMSSB (limiting cysteine modified Stainer-Scholte batch) culture system consisted of B. Pertussis grown in batch mode using the media as shown in Table 2 below. Briefly, "batch mode" is a process whereby micro-organisms are cultured in a single culture medium, usually liquid or semi-liquid, without replenishing or exchanging a significant amount of the spent, or used, culture media. In the present invention batch mode cultures (LCMSSB) were incubated aerobically at between approximately 35° C. and 37° C. until bacterial optical densities reached >1.0 absorbance units as measured spectrophotometrically at 600 nm using procedures known to those skilled in the art. The second culture systems LCMSSFB (limiting cysteine modified Stainer-Scholte fed batch) was maintained using the culture media disclosed in Table 3. Note that no cysteine was added to the basal media. Instead, L-cysteine was added at a rate of 20 mg/hour for the entire incubation period. The final culture system was designated LCMSSBa (limiting cysteine modified Stainer-Scholte batch plus $BaCl_2$) and used the basal media depicted in Table 2.

All three culture systems were inoculated and maintained as follows: Bordetella cultures were incubated at between approximately 35° C. and 37° C. in 20 liter bioreactors (New Brunswick BioFlo IV® (New Brunswick Scientific, Edison N.J.) connected to an AFS Biocommand v2.0 (New Brunswick Scientific, Edison N.J.) which collected data for pH, agitation, dissolved oxygen, temperature, and air flow rate. Additional pumps for anti-foam agents and pH control reagents were added as needed as known to those of ordinary skill in the art. Airflow was adjusted to 4.0 liters per minute, dissolved oxygen was maintained at 40% and pH was maintained at approximately 7.2.

Each 20-liter bioreactor contained 11 liters of test media and was inoculated with one liter of actively growing bacterial starter culture. The actively growing started cultures were prepared by inoculating shaker flasks containing one liter of Stainer Scholte (SS) medium, the formula of which is depicted in Tables 5 and 6, with frozen seed and incubated until an optical density of >1.0 $OD_{600}$ was reached (approximately 20–24 hours).

The inoculated fermentors were sampled at 3–6 hour intervals and separated into culture supernatants and cell pellets using centrifugation. The culture supernatants were assayed for PT, sulfates, organic acids, amino acids and bacterial density. Bacterial cell pellets were analyzed for internal sulfate and PT concentrations. Each culture system received a specific supplement(s) when culture bacterial population densities reached approximately >1.0 absorbance units (approximately 12 hours post inoculation). Both LCMSSB and LCMSSBa received 200 mL of the amino acid supplement described in Table 4 below in addition to 10.0 mg/L $FeSO_4.7H_2O$ and 5.0 g/L monosodium glutamate (the $FeSO_4$/glutamate supplement). The LCMSSBa culture also received sufficient 1 mM $BaCl_2$ to obtain a final culture media concentration of 20 nM $BaCl_2$; the LCMSSFB cultures received the $FeSO_4$/glutamate supplement with additional amino acids excluding cysteine and no $BaCl_2$. After supplementation, the fermentors were incubated as before until the experiments were terminated.

TABLE 2

Components of the LCMSSB Medium.

| Component | Amount (g/L) |
|---|---|
| Sodium Chloride | 2.5 |
| $KH_2PO_4$ | 0.5 |
| KCl | 0.2 |
| $MgCl_2.6H_2O$ | 0.1 |
| $CaCl_2$ | 0.02 |
| TRIS Base | 1.525 |
| Ascorbic Acid | 0.02 |
| Glutathione | 0.10 |
| L-Cysteine Monohydrochloride | 0.04 |
| $FeSO_4.7H_2O$ | 0.0010 |
| Niacin | 0.004 |
| L-Arginine Monohydrochloride | 0.40 |
| L-Asparagine | 0.10 |
| L-Aspartic Acid | 0.04 |
| L-Histidine | 0.03 |
| L-Isoleucine | 0.10 |
| L-Leucine | 0.10 |
| L-Lysine Monohydrochloride | 0.08 |
| L-Methionine | 0.03 |
| L-Phenylalanine | 0.03 |
| L-Serine | 0.06 |
| L-Threonine | 0.04 |
| L-Tryptophan | 0.01 |
| L-Valine | 0.04 |

TABLE 3

Components of the LCMSSFB Medium.

| Component | Amount (g/L) |
|---|---|
| Sodium Chloride | 2.5 |
| $KH_2PO_4$ | 0.5 |
| KCl | 0.2 |
| $MgCl_2.6H_2O$ | 0.1 |
| $CaCl_2$ | 0.02 |
| TRIS Base | 1.525 |
| Ascorbic Acid | 0.02 |
| Glutathione | 0.10 |
| $FeSO_4.7H_2O$ | 0.0010 |
| Niacin | 0.004 |
| L-Arginine Monohydrochloride | 0.40 |
| L-Asparagine | 0.10 |
| L-Aspartic Acid | 0.04 |
| L-Histidine | 0.03 |
| L-Isoleucine | 0.10 |
| L-Leucine | 0.10 |
| L-Lysine Monohydrochloride | 0.08 |
| L-Methionine | 0.03 |
| L-Phenylalanine | 0.03 |
| L-Serine | 0.06 |
| L-Threonine | 0.04 |
| L-Tryptophan | 0.01 |
| L-Valine | 0.04 |

TABLE 4

Components of the Amino Acid Supplement

| | |
|---|---|
| L-Cysteine Monohydrochloride | 0.05 |
| L-Arginine Monohydrochloride | 0.40 |
| L-Asparagine | 0.10 |
| L-Aspartic Acid | 0.04 |
| L-Histidine | 0.03 |
| L-Isoleucine | 0.10 |
| L-Leucine | 0.10 |
| L-Lysine Monohydrochloride | 0.08 |
| L-Methionine | 0.03 |
| L-Phenylalanine | 0.03 |
| L-Serine | 0.06 |
| L-Threonine | 0.04 |
| L-Tryptophan | 0.01 |
| L-Valine | 0.04 |

Figure 8A:
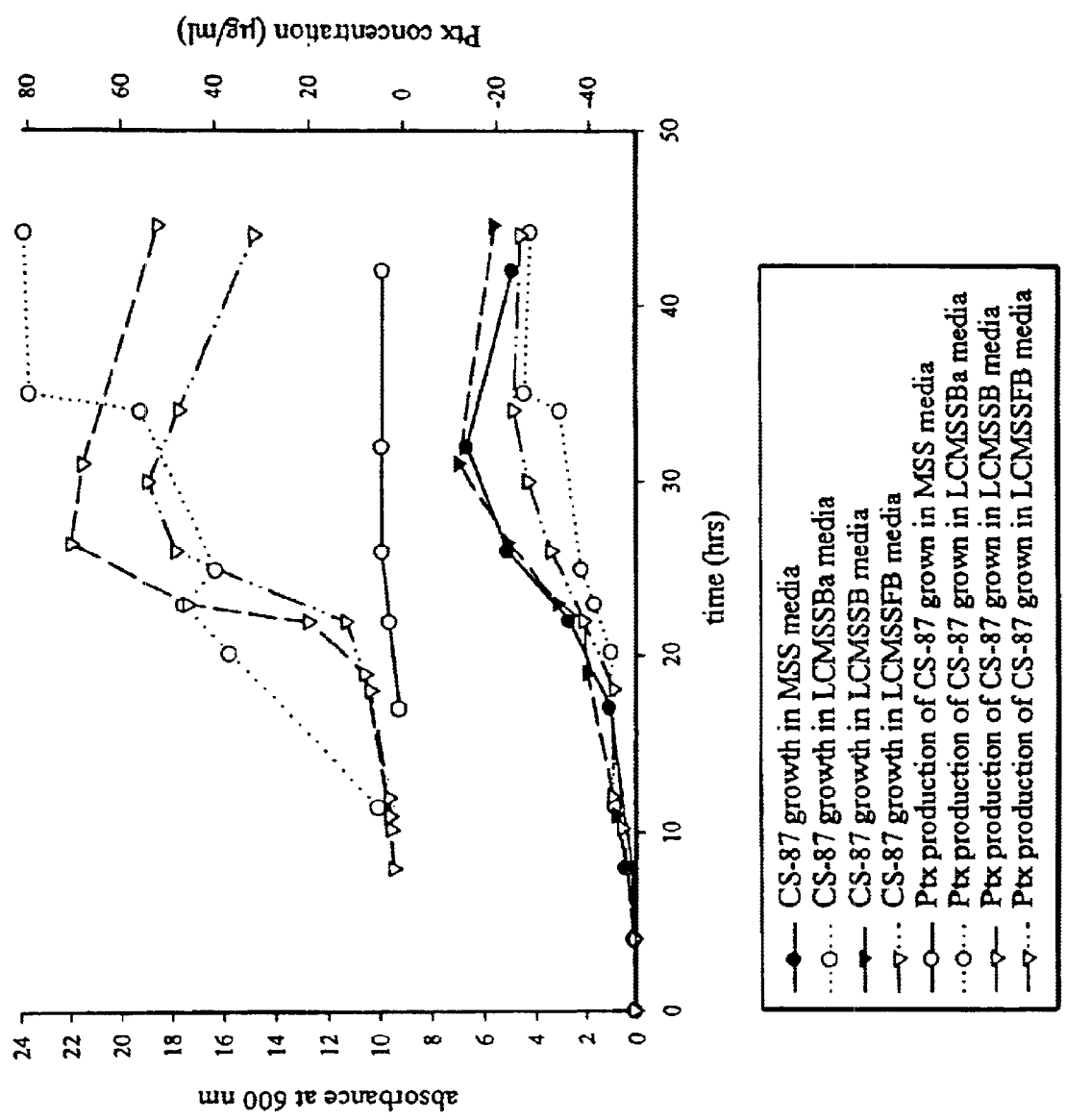
FIG. 8a: Graphically depicts total B pertussis toxin production in 20 liter fermentors under limiting cysteine conditions measure at 600 nm absorbance.
Figure 8B:
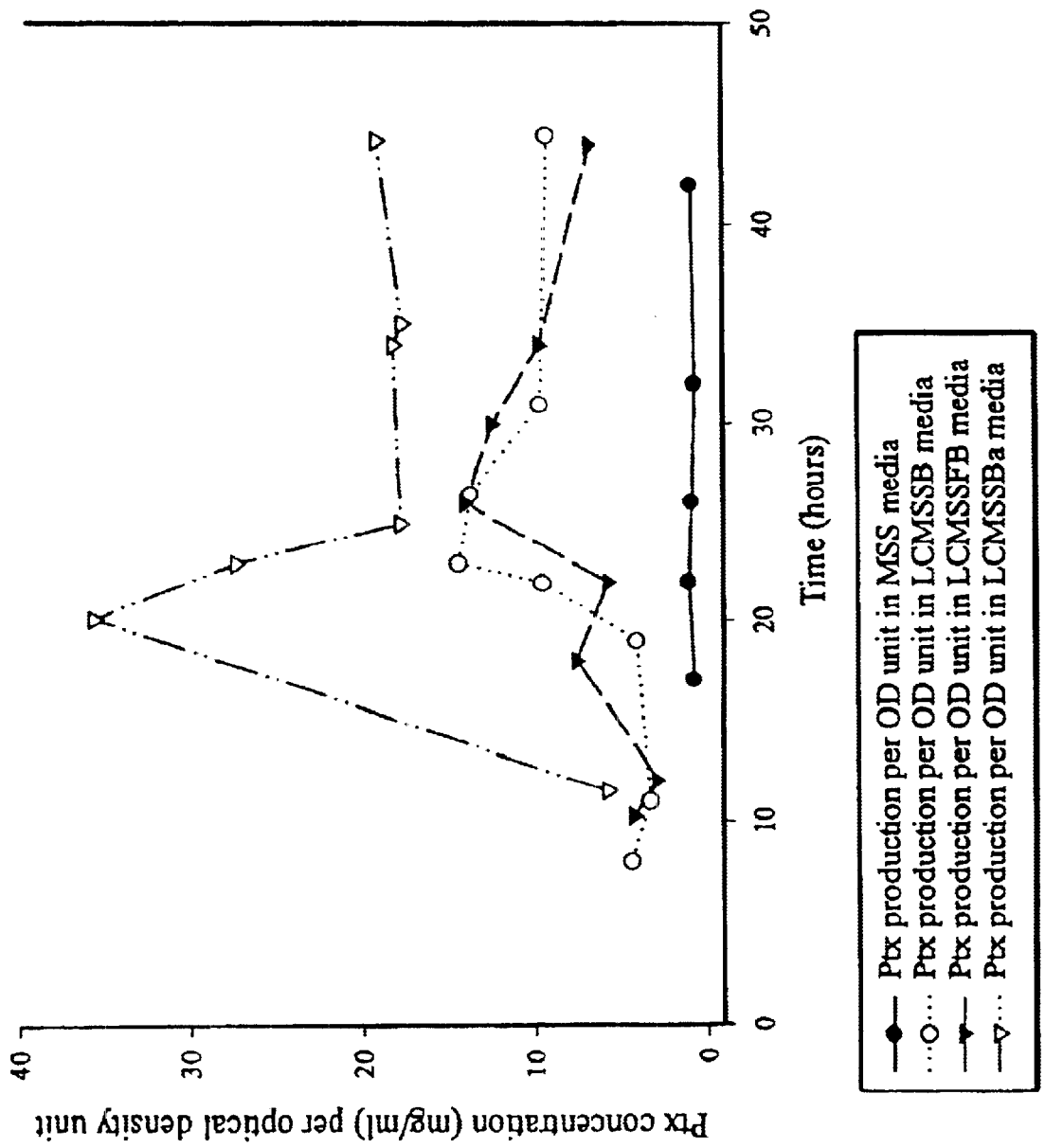
FIG. 8b: Graphically depicts B pertussis toxin production in 20 liter fermentors under limiting cysteine conditions measured as mg/mL of toxin per optical density unit.
Figure 9:
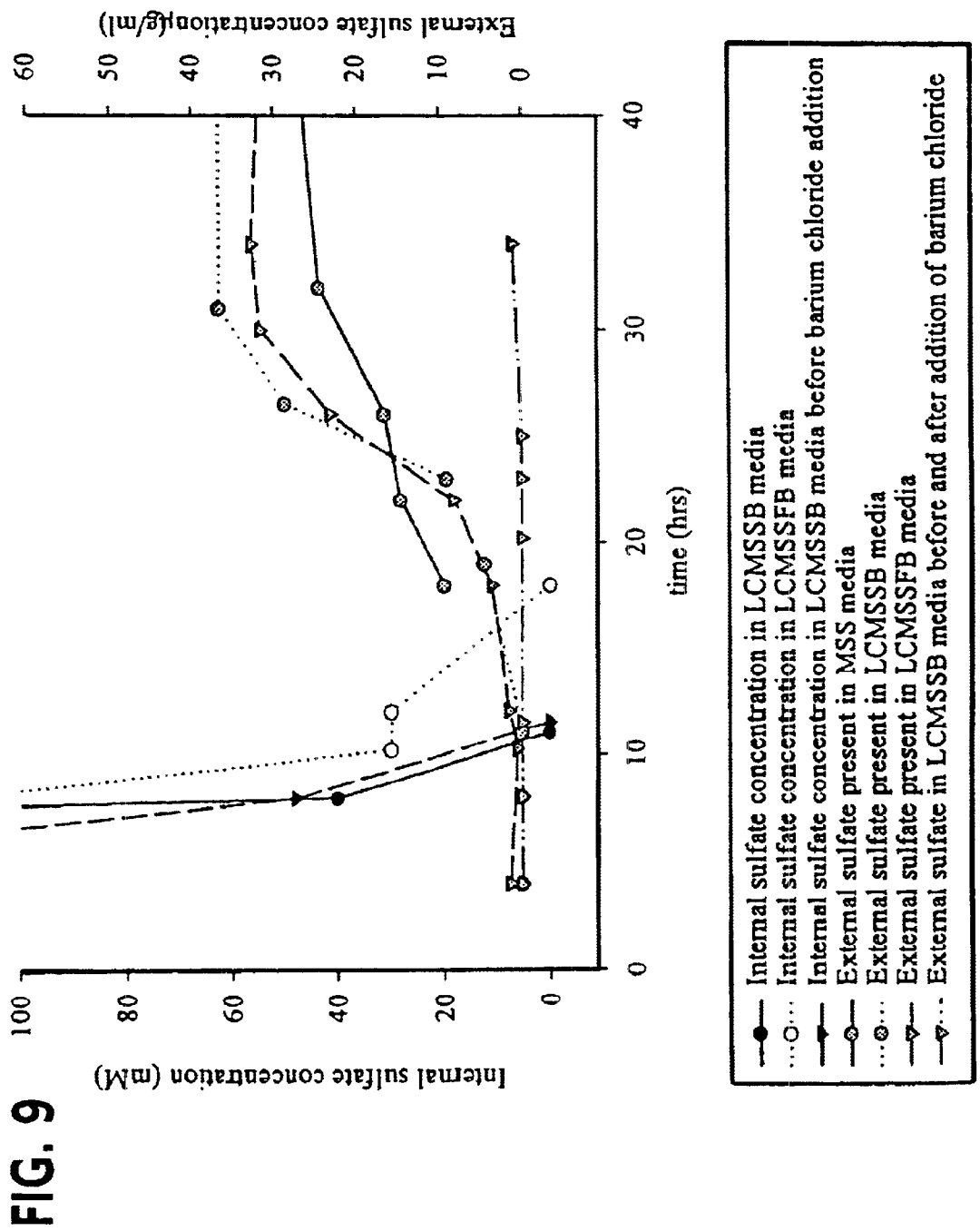
FIG. 9: Graphically depicts internal and external sulfate concentrations in B. Pertussis cells in 20 liter fermentors in limiting cysteine conditions.

All three reduced cysteine culture systems (LCMSSB, LCMSSFB and LCMSSBa) were tested in parallel with conventional SS media having cysteine concentrations as known in the prior art. Bordetella bacterial and PT concentrations are graphically depicted in FIGS. 8a and 8b. It can be seen from FIG. 8a that maximum Bordetella cell concentrations were reached at approximately 32 hours. Maximum growth was nearly identical when normal PT production media is compared with modified SS in batch mode. FIG. 8b depicts maximum PT production as measure in mg/ml of culture media. It is readily apparent that a significant improvement in overall PT production is realized using any of the cysteine limiting culture systems of the present invention when compared to conventional culture systems. Moreover, FIG. 9 depicts internal and external sulfate concentrations in B. Pertussis cells in 20 liter fermentors in limiting cysteine conditions. The LCMSSBa culture system demonstrated the best improvement in overall PT production. Therefore, as theorized by the present inventors, PT production can be significantly improved by limiting the amount of inhibitor precursor in the culture media. Moreover, even further improvement can be realized when the precursor limiting culture systems of the present invention are combined with the toxin expression inhibitor removal systems of the present invention.

The present inventors have demonstrated that: 1) specific toxin expression inhibitors that accumulate in the media of toxin producing bacteria can significantly reduce overall toxin production; and 2) that removal of toxin expression inhibitors from the culture media, or reduction in toxin inhibitor formation by reducing inhibitor precursors in the culture media, can significantly increase overall toxin production. Therefore, the present inventors theorized that genetically disabling a toxin producing organism's ability to produce a toxin expression inhibitor might yield similar increases in overall toxin production. Consequently, in yet another embodiment of the present invention a recombinant B. Pertussis lacking cysteine desulfinase activity ("knockout mutant") that does not produce sulfate in culture and, thus, does not exhibit inhibited PT expression is provided. Such knockout mutants may be prepared by anyone of a number of different methods. See, for example, U.S. Pat. Nos. 5,557,032 and 5,614,396. Such methods, in general, involve homologous recombination of a DNA construct with B. Pertussis chromosomal DNA. Homologous recombination is a well-studied, natural cellular process which results in the scission of two nucleic acid molecules having identical or substantially similar sequences (i.e. homologous), and the ligation of the two molecules such that one region of each initially present molecule is ligated to a region of the other molecule. (See Sedivy, J. M., BioTechnol. 6:1192–1196 (1988)). Homologous recombination is, thus, a sequence specific process by which cells can transfer a "region" of DNA from one DNA molecule to another. For homologous recombination to occur between two DNA molecules, the molecules must possess a "region of homology" with respect to one another. Such a region of homology must be at least two base pairs long. Two DNA molecules possess a region of homology when one contains a region whose sequence is so similar to a region in the second molecule that homologous recombination can occur. Where a particular region is flanked by two regions of homology, then two recombination events may occur, resulting in an exchange of regions between the two recombining molecules. Homologous recombination is catalyzed by enzymes that are naturally present in B. Pertussis.

In one such method, the gene coding for cysteine desulfinase (FIG. 7), e.g. contained within a plasmid, is cut with restriction enzymes selected to cut within the gene such that a new DNA sequence encoding a marker gene can be inserted within the cysteine desulfinase gene sequence. This marker gene will serve to prevent expression of the cysteine desulfinase gene. The marker gene can be any nucleic acid sequence that is detectable and/or assayable, however, in a preferred embodiment, it is an antibiotic resistance gene. The marker gene may be operably linked to its own promoter or to another strong promoter from any source that will be active or easily activatable in B. Pertussis. In another embodiment, the marker gene may be transcribed using the promoter of the cysteine desulfinase gene. The marker gene may have a poly A sequence attached to the 3'-end of the gene to terminate transcription. Preferred marker genes include any antibiotic resistance gene such as ermC' (the erythromycin resistance gene), neo (the neomycin resistance gene), amp (the ampicillin resistance gene), kan (the kanamycin resistance gene) and gent (the gentamicin resistance gene).

After the DNA sequence has been digested with the appropriate restriction enzymes, e.g. SpII and SphI or PstI and PvoI, the marker gene sequence is ligated into the cysteine desulfinase DNA sequence using methods well known to the skilled artisan and disclosed, for example, in Sambrook et al. (Molecular Cloning: A Laboratory Manual, Cold Spring Harbor Laboratory Press, Cold Spring Harbor, N.Y. (1989)). The ends of the DNA fragments to be ligated must be compatible; this is achieved by either cutting all fragments with enzymes that generate compatible ends, or by blunting the ends prior to ligation. Blunting is done using methods well known in the art, such as for example, by use of Klenow fragment (DNA polymerase I) or other DNA polymerase to fill in sticky ends. This construct contains DNA sequences corresponding to defined regions of the cysteine desulfinase gene, e.g. corresponding to the 3'- and 5'-ends of the cysteine desulfinase gene, allowing for integration of the construct by homologous recombination. This DNA construct may be ligated into a plasmid having a second antibiotic resistance gene.

The construct may then be transfected into B. Pertussis using known methods, e.g. by electroporation or by mating with transfected E. coli cells. Screening of the cells is accomplished by culturing the cells in the presence of otherwise lethal concentrations of one or more antibiotics corresponding to the antibiotic resistance genes that are present. Those cells that survive will have the knockout construct integrated therein. One may use a non-replicating plasmid so that the selected cells would not just have the plasmid construct therein. In order to confirm the integration of the knockout construct, a Southern Blot of the B. Pertussis DNA can be probed with a sequence designed to hybridize only to the marker sequence and/or the portion of the cysteine desulfinase that is removed. Alternatively or additionally, the DNA can be amplified by PCR with probes corresponding to the 3'- and 5'-ends of the cysteine desulfinase gene. Finally, cysteine desulfinase activity may be assayed.

In another embodiment, B. Pertussis may be cultivated in the presence of nucleotide sequences that are anti-sense to the coding sequence of the cysteine desulfinase gene. In this embodiment, the nucleotide sequences are taken up by B. Pertussis, hybridize to the cysteine desulfinase-encoding gene, and inhibit translation of the gene. Modified nucleotide sequences can also be employed which interact with the bases of the gene to form covalent bonds and thereby inhibit translation. See U.S. Pat. No. 6,015,676.

Examples of nucleotides which are antisense to the cysteine desulfinase gene include any nucleotide of at least 8 bases, preferably, 10 to 15 bases, which are complementary to the coding region of FIG. 7. Examples include:

GATTGCTGAT (SEQ. ID. NO. 1)

TAGATGGGGC (SEQ. ID. NO. 2)

In the present invention, a variety of media may be used to cultivate B. Pertussis. Non-limiting, exemplary media include the Stainer Scholte and the GMAR modified media. The components of the Stainer Scholte and GMAR modified media are presented in Tables 2 and 3, respectively.

TABLE 5

Components of the Stainer Scholte Medium.[b]

| Component | Amount (g/L) |
|---|---|
| L-Glutamic Acid Monosodium Salt | 10.72 |
| L-Proline | 0.24 |
| Sodium Chloride | 2.5 |
| $KH_2PO_4$ | 0.5 |
| KCl | 0.2 |

TABLE 5-continued

Components of the Stainer Scholte Medium.[b]

| Component | Amount (g/L) |
|---|---|
| $MgCl_2.6H_2O$ | 0.1 |
| $CaCl_2$ | 0.02 |
| TRIS Base | 1.525 |
| Ascorbic Acid | 0.02 |
| Glutathione | 0.10 |
| L-Cysteine | 0.04 |
| Nicotinic Acid | 0.004 |
| $FeSO_4.7H_2O$ | 0.010 |

[b]From: Hewlett and Wolff, J. Bacteriol. 127:890–898 (1976).

TABLE 6

Components of the GMAR Modified Medium.

| Component | Amount (g/L) |
|---|---|
| L-Glutamic Acid Monosodium Salt | 10.7 |
| L-Proline | 0.24 |
| Sodium Chloride | 2.50 |
| $KH_2PO_4$ | 0.50 |
| KCl | 0.20 |
| $MgCl_2.6H_2O$ | 0.10 |
| $CaCl_2.2H_2O$ | 0.02 |
| TRIS Base | 1.52 |
| Ascorbic Acid | 0.02 |
| Glutathione, Reduced | 0.10 |
| L-Cysteine | 0.04 |
| Niacin | 0.004 |
| $FeSO_4.7H_2O$ | 0.001 |
| L-Arginine Monohydrochloride | 0.40 |
| L-Asparagine | 0.10 |
| L-Aspartic Acid | 0.04 |
| L-Cysteine Monohydrochloride | 0.10 |
| L-Histidine | 0.03 |
| L-Isoleucine | 0.10 |
| L-Leucine | 0.10 |
| L-Lysine Monohydrochloride | 0.08 |
| L-Methionine | 0.03 |
| L-Phenylalanine | 0.03 |
| L-Serine | 0.06 |
| L-Threonine | 0.04 |
| L-Tryptophan | 0.01 |
| L-Valine | 0.04 |

The PT toxin produced by the methods of the current invention may be purified according to the method described by Sekura et al., J. Biol. Chem. 258:14647–14651 (1983). Briefly, the method of Sekura utilizes two consecutive chromatographic steps to purify PT. The first step involves chromatography on an Affi-gel blue column. The second step involves chromatography on a fetuin-agarose column. The PT purification method of Sekura et al. allows for the routine and rapid purification of PT in relatively large quantities (in excess of 10 mg). Alternatively, PT may be purified using a peptide affinity column. Such a column is described below in Example 1. In this embodiment, the PT is adsorbed onto the column, washed with buffer (e.g. 50 mM TRIS HCl, pH=6.2), and the PT is then eluted with 4 M $MgCl_2$. The $MgCl_2$ is removed by dialysis to give substantially pure PT.

Having now generally described this invention, the same will be understood by reference to the following examples which are provided herein for purposes of illustration only and are not intended to be limiting unless otherwise specified.

EXAMPLE 1

Materials and Methods

Organisms: Wild-type *B. Pertussis* strain CS87 was used for most of these studies. This strain originated in China and was brought to the National Institute of Child Health and Human Development (NICHD) at the National Institutes of Health (NIH). In addition, several strains of BP were procured from the American Type Culture Collection (Manassas, Va.), including, but not limited to ATCC number 10380 both of which are suitable for preparing the cysteine desulfinase knockout mutants disclosed herein. Organisms were stored at −70° C. or maintained on BGA (BBL, Inc. Rockville, Md.) in a humid incubator maintained at 37° C.

The medium utilized to culture the cells was similar to the defined medium described by Stainer and Scholte. J. Gen. Microbiol. 63:211–220 (1970). One liter of the medium contained: 10.7 g monosodium glutamate, 0.24 g proline, 2.5 g NaCl, 0.5 g $KH_2PO_4$, 0.2 g KCl, 0.1 g $MgCl_2.6H_2O$, 20 mg $CaCl_2.2H_2O$, 1.52 g Tris, 20 mg ascorbic acid, 100 mg glutathione, 40 mg cysteine, and 4 mg niacin. The salts, glutamate, and proline were prepared as a basal formulation and were autoclaved for sterilization. The rest of the medium (supplement) was prepared in concentrated form (100-fold) and filter sterilized. The final pH of the medium was between 7.2 and 7.5. In some experiments, 10 mg/L $FeSO_4.7H_2O$ was added. Organisms were grown either in triple baffled Erlenmeyer flasks in a New Brunswick Innova Model 4300 shaking incubator (New Brunswick Scientific, Edison, N.J.) maintained at 37° C. or in a New Brunswick 20 L BioFlo IV (New Brunswick Scientific) running in batch mode with a working volume of 12 L. The reactor was connected to an AFS Bio Command v.2.0 (New Brunswick Scientific), which collected data for pH, agitation, dissolved oxygen, temperature, air flow rate and additional pumps for antifoam and pH maintenance. The air flow rate in the fermentor was set at 0.125 vvm and the temperature was controlled at 36.5° C. in all experiments. The dissolved oxygen (DO) was maintained at 40% by using an agitation cascade from 150 to 1000 RPM. The pH was controlled at 7.2 by the addition of 50% $H_3PO_4$.

The reactor was batched with approximately 11 L of defined medium and inoculated with an actively growing seed (1 L), for a total working volume of 12 L. Samples were drawn from the resterilization sample port every 3 to 6 hours. For analysis of extracellular metabolites, the supernatant was filtered through a 0.2 μm Millex-GV filter (Millipore Co., Bedford, Mass.) and stored at −20° C.

Growth of the culture was measured by optical density at 650 nm ($OD_{650}$) using a Shimadzu UV Spec 120 (Shimadzu, Columbia, Md.). Culture purity was verified by gram staining and plating on BGA (BBL, Inc. Rockville, Md.) and trypticase soy agar (TSA; BBL, Inc.). A pure culture of *B. Pertussis* would demonstrate all organisms staining gram-negative, growth on BGA agar and lack of growth on TSA agar.

Amino acid analysis: The analysis and quantification of amino acids were made by reverse phase high-pressure liquid chromatography (RP-HPLC) using an on-line pre-column derivatization, as provided for the AminoQuant column (Hewlett-Packard Co., Wilmington, Del.). Primary acids were derivatized by the OPA reagent (10 mg/ml o-phtalaldehyde, 10 mg/ml 3-mercaptopropionic acid in 0.4 M borate buffer), while secondary amino acids were derivatized by FMOC reagent (2.5 mg/ml 9-fluorenylmethylchloroformate in acetonitrile). For primary amino acids, the mobile phase consisted of sodium acetate/tri-ethanolamine/tetrahydrofuran (pH 7.2±0.05) and were detected at 338 nm. Secondary amino acids were eluted using a sodium acetate/methanol/acetonitrile mobile phase (pH 7.2±0.05) and were detected at 262 nm. The identification of each amino acid was performed with a set of amino acid standards (Hewlett-Packard) at different concentrations (100, 250, and 1000 pmol/μl). HPLC Model HP-1050 (Hewlett-Packard) was utilized for these analyses in conjunction with the HP ChemStation software (Hewlett-Packard, v.2.0).

Organic Acid detection and quantification: Organic acids were detected using a Model HP-1050 HPLC (Hewlett-Packard) in conjunction with the HP ChemStation v.2.0 software and equipped with a BioRad Aminex HPX-87H column (Bio-Rad Laboratories, Burlingame, Calif.) having a mobile gas phase of 4 mM $H_2SO_4$. The column was equilibrated at 35° C. and the isocratic flow rate was 0.6 ml/min. The detection was performed at 215 nm. The identification of each organic acid was achieved by injecting the Bio-Rad Organic Acid Analysis Standard (Bio-Rad Laboratories), which consisted of a mixture of sodium oxalate, sodium citrate, sodium maleate, sodium succinate, sodium formate, and sodium acetate. Pyruvate was assessed by spiking the organic acid standard with 2.5 g/l pyruvate.

Each of the organic acids were quantified using enzymatic kits and following the manufacturer's recommended protocol as follows: Citric acid, Boehringer-Mannheim kit 139–076 (Boehringer-Mannheim, Indianapolis, Ind.); succinic acid, Boehringer-Mannheim kit 176–281 (Boehringer-Mannheim, Indianapolis, Ind.); formic acid, Boehringer-Mannheim kit 979–732 (Boehringer-Mannheim, Indianapolis, Ind.); acetic acid, Boehringer-Mannheim kit 148–261 (Boehringer-Mannheim, Indianapolis, Ind.); oxalic acid, Boehringer-Mannheim kit 755–699 (Boehringer-Mannheim, Indianapolis, Ind.); and pyruvate, Sigma kit 726-UV (Sigma Chemicals Co, St. Louis, Mo.).

Quantitative PT ELISA Assay: Microtiter plates (Nunc-Immuno Plate IIF, Vangard International, Neptune, N.J.) were sensitized by adding 0.1 ml per well of fetuin (Sigma Chemical Co.) at 0.2 μg/ml in 0.1 M sodium carbonate, pH 9.6, and incubating overnight at room temperature. The plates were washed five times with a solution containing 0.9% NaCl, 0.05% Brij 35, 10 mM sodium acetate at pH 7.0, and 0.02% azide. Samples containing PT were diluted in PBS with 0.5% Brij 35 and added to the plate and incubated for 2 hr at room temperature. The plates were again washed as before and the monoclonal antibody to PT (20.6) was diluted with PBS. Ibsen, et al., Infect. Immun. 61:2408–2418 (1993). The plates were again washed and the secondary antibody, alkaline phosphatase conjugated goat anti-mouse IgG and IgM (Tago Inc., Burlingame, Calif.), was diluted in PBS-Brij, was added to the plates and was then incubated for 2 h at room temperature. The plates were washed as before and p-nitrophenyl phosphate (Sigma Phosphatase Substrate 104) (1 mg/ml), in a solution of 0.1 M diethanolamine, 1 mM $MgCl_2$, 0.1 mM $ZnCl_2$, and 0.02% azide, at pH 9.8, was added. The plates were incubated at 37° C. for 1 h and the absorbance at 405 nm was determined using a Dynex Model MRX microtiter plate reader (Dynex Technologies, Inc., Chantilly, Va.). For each plate, a standard curve was generated using purified PT (North American Vaccine, Inc.) diluted in 0.1% BSA and 0.1% glycerol in PBS. The concentration of PT from culture samples was calculated from the standard curve.

Sulfate Determinations: Sulfate concentrations within the medium were determined using the methods of Melnicoff, et al. The assay was adapted to a microplate assay. Melnicoff, et al., Res. Commun. Chem. Pathol. Pharmacol. 14:377–386 (1976).

Cloning of the B. Pertussis nifS-like gene: The DNA fragment containing the nifS-like gene was amplified by a Perkin-Elmer Thermal Cycler 480. The reaction mixture (50 µl) contained: 20 ng purified B. Pertussis chromosomal DNA, 0.2 µM of each primer (forward primer: 5' ATG AGC MT CGC CCC ATC TAC 3' (SEQ. ID. NO. 3); reversed primer: 5' CAC TAT TTG GTC GGT CGG 3' (SEQ. ID. NO.4), 2 mM $MgCl_2$, 10 mM Tris-HCl (pH 8.3), 50 mM KCl, 400 µM each dNTP, and 2.5 units of AmpliTaq Gold (Perkin Elmer, Branchburg, N.J.). The conditions were as follows: first cycle, 2 min at 94° C.; subsequent 35 cycles, 94° C. (2 min), 42° C. (1 min), 72° C. (2 min); and with a final 72° C. incubation time for 8 min. The PCR product was gel purified in a 1% agarose gel and ligated into pCR®II-TOPO (Invitrogen, Calrsbad, Calif.) using the conditions recommended by the manufacturer making pBPfilS. The plasmid pBPfilS was transformed into E. coli strain TOPF' (Invirtogen) and transformants were selected on LB-amp agar media. Sequencing was performed using an Applied Biosystems PRISM Model 310 Automated sequencer (Applied Biosystems, Inc., Foster City, Calif.) using the manufacturer's recommendations and sequencing kit.

Construction of a B. Pertussis strain containing a null mutation in the BP filS-like gene: The pBPfilS plasmid made in accordance with the teachings of the present invention was cut with SplI and SphI as well as blunting the ends with the Klenow fragment of DNA polymerase (Boehringer Mannheim). The cut plasmid was gel purified and a blunt-ended erythromycin resistant gene (ermC') or luciferase was ligated into the plasmid construction. Klugman, et al. Infect. Immun. 57:2066–2071 (1989). Transformants of DH5 were identified having resistance to 100 $\mu$g of erythromycin per ml. The constructed plasmid was reisolated using Qiagen columns (Qiagen, Inc., Valencia, Calif.) and the mutated insert was isolated by cutting the plasmid with BamHI and XhoI. The insert was gel purified and ligated into the BamHI and XhoI site of plasmid pSS1129 to make pBPΔfilS. Stibitz, J. Bacteriol. 180:2484–2492 (1998). This was transformed into *E. coli* strain SM10 and the transformants used to mate with *B. Pertussis* strain BP536 as described by Stibitz. "Use of Conditionally Counterselectable Suicide Vectors for Allelic Exchange," in Bacterial Pathogenesis, Clark and Bavoil (eds.), p.301–308 (1997). *B. Pertussis* isolates containing the null BpfilS gene within the chromosome were selected for gentamicin, streptomycin and/or erythromycin resistance or luciferase activity on BGA agar.

Miscellaneous: All materials were purchased from Sigma Chemical Co. and/or of the highest grade available. Total protein was quantified by Coomassie Protein Assay®(Pierce Chemical Co., Rockford, Ill.). Human IgG was used as the standard. Bordetella pertussis strain BP536, a spontaneous streptomycin resistant mutant of strain BP 338 used in the transformation experiments was obtained from Dr. Scott Stibitz at the Center for Biological Research and Evaluation, United States Food and Drug Administration (Stibitz, S. and M-S. Yang. 1991. J. Bact. 173: 4288–4296). The transformed *B. pertussis* knockout mutant derived therefrom was designated strain BP536pWY and has been deposited with the American Type Culture Collection, (Manassas, Va.) in accordance with the terms of the Budapest Treaty. The American Type Culture Collection has assigned *B. Pertissis* strain BP536pWY ATCC number PTA-3254. All methods employed are well known to those of ordinary skill in the art. See for example: Methods in Molecular Biology, vol XX, B. D. Shepard and M. S. Gilmore (Eds) (1995); DNA sequencing, L. Alphey. Bios Scientific Publishers (1997); Diagnostic and Molecular Biology: Principles and Applications, D. H. Persing, T. F. Smith, F. C. Tenover and T. J. White (eds) (1993) American Society for Molecular Biology; Molecular Biology, D. Freifelder (ed) (1987) Jones and Bartlett Publishers; and Molecular Biology of the Gene, J. D. Watson, N. H. Hopkins, J. W. Roberts, J. A. Steiz and A. M. Weiner (eds) (1987) The Bengerman/Cummings Publishing Company, Inc.

Results

Detection of Inhibitor(s) of PT production in broth cultures of BP: Samples were taken at various times during the growth phase of the BP cultures. The samples were monitored for BP growth by measuring the $OD_{650}$ and for the production of PT by ELISA. The results were calculated as PT in microgram/per ml/$OD_{650}$ in order to approximate the amount of PT produced per cell. As shown in FIG. 1, the amount of PT produced per cell fell drastically midway through the growth cycle. Although *B. Pertussis* continued in logarithmic phase growth, the production of PT appeared to decrease almost to the total elimination of PT production. This suggested that an inhibitor of PT production was being generated during the early phases of the culture and that after reaching inhibitory concentration, PT production ceased. To test this hypothesis, culture supernatant from a *B. Pertussis* culture grown to stationary phase was lyophilized and was reconstituted with growth media lacking the basic salts. This mixture was then used to grow a second culture of *B. Pertussis* and was compared to the original media used for *B. Pertussis*. Samples were taken and assayed as before. The growth of *B. Pertussis* in each of the two media was similar with the $OD_{650}$ reaching approximately the same levels. However, the total amount of PT produced in the reconstituted mixture was drastically reduced compared to that in the original media. A more visual demonstration of such an inhibition, and that this inhibitor also effects the production of adenylate cyclase, the cause of haemolysis on blood agar plate, is shown in FIG. 2. An initial streak of *B. Pertussis* was made on a BGA plate and allowed to grow for 48 hrs. Secondary cross-streaks were then made and the agar plate was incubated for an additional 48 hrs. It can be seen that a zone of non-haemolysis radiates out from the initial growth streak. Characterization of the inhibitor began by filtering the spent culture media through a 3,000 MWCO filter retaining both the permeate and the filtrate. Both were lyophilized and reconstituted as before. FIG. 3 demonstrates the results of the *B. Pertussis* grown in these mixtures as compared to the GMAR media. The production of PT was inhibited by the permeate mixture suggesting that the inhibitor had a molecular weigh smaller than 3,000.

Amino Acid and Organic Acid Analysis: Both amino acid and organic acid analysis were performed on samples taken at different times during the course of a typical *B. Pertussis* culture in order to determine whether the rise and/or the timing of the increase in these compounds correlated with the timing of the production inhibition of PT. These data are shown in FIGS. 4*a* and 4*b*. It should be noted that the drop in PT production occurs at approximately half way through the growth phase, typically at 20 h. Three compounds appear and continue to increase in concentration around this time period: methionine, cysteine, and pyruvic acid. The rise in methionine seems to occur first, followed by cysteine and pyruvic acid. Many pathways link the metabolism of methionine to cysteine. However, few pathways generate pyruvate from cysteine. Three such pathways are shown in Leninger, A. L., Biochemistry, Worth Publishers, pp.441 (1970). In each of these three pathways, the sulfur group of cysteine is removed and pyruvate is generated thereby linking the rise of each of these compounds with each other as well as to an increase of sulfate within the media.

Figure 4A:
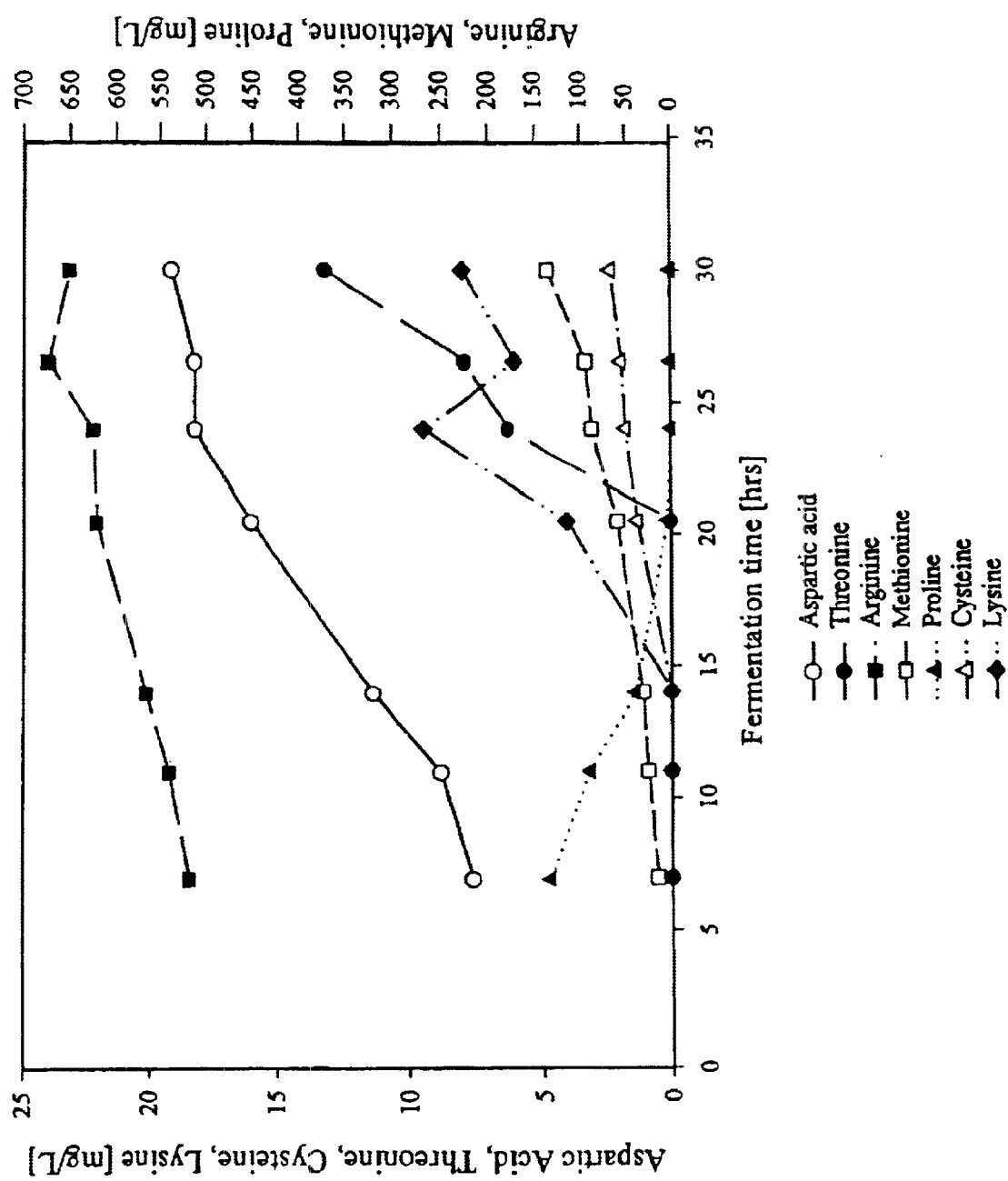
FIG. 4A: Graph of fermentation time (hours) vs. aspartic acid, threonine cysteine and lysine concentration (mg/L) and arginine, methionine and proline concentration (mg/L) demonstrating the amino acid profiles during fermentation.
Figure 4B:
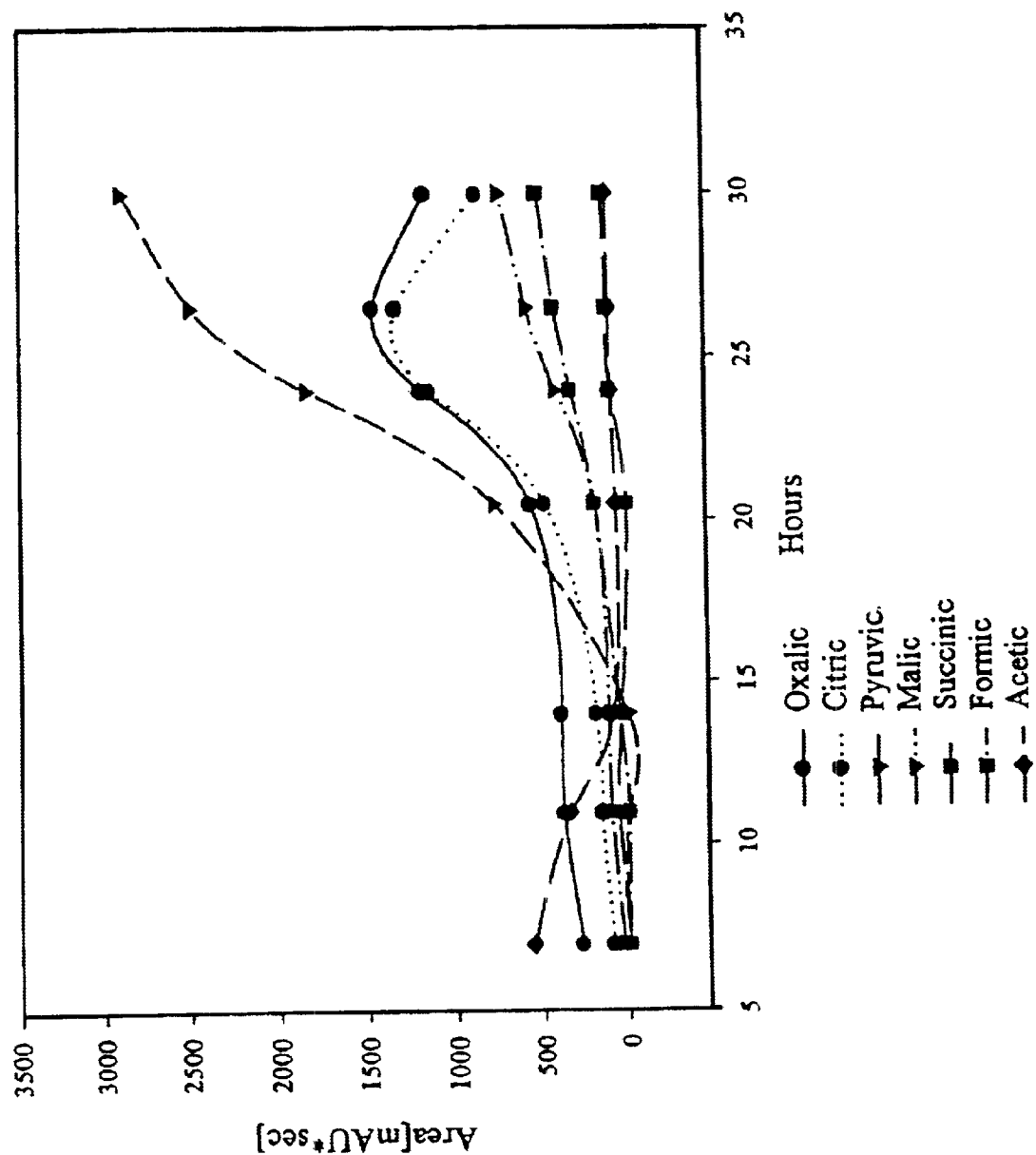
FIG. 4B: Graph of time (hours) vs. area (mAU☐sec) demonstrating changes in the organic acid concentrations as a function of fermentation time.
Figure 5:
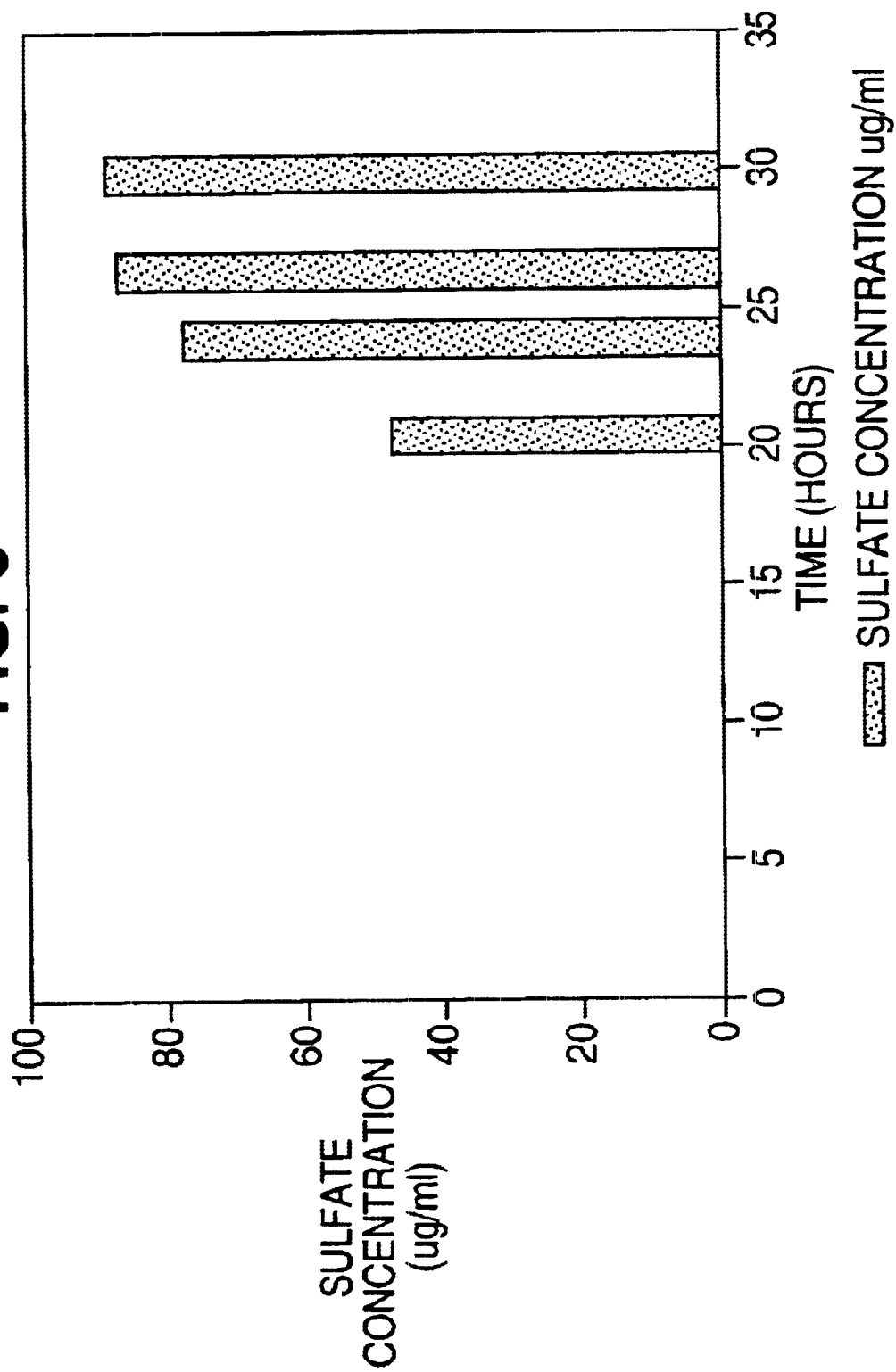
FIG. 5: Bar graph showing sulfate concentration ($\mu$g/mL) at various culture times.

Sulfate Production within *B. Pertussis* culture: The concentration of sulfate was determined on each of the culture samples and compared with *B. Pertussis* growth ($OD_{650}$) and time. FIG. 5 illustrates the results of these determinations on the same samples used to generate the data in FIG. 4. The data demonstrate that at the approximate time when methionine, cysteine, and finally pyruvate increased in concentration, there was also a large increase in the production of sulfate.

Growth of *B. Pertussis* and the production of PT in the presence of $BaCl_2$: The sulfate ion is a modulator of *B. Pertussis* from the virulent phase to the avirulent phase. This modulation is regulated by the proteins BvgS and BvgA which are members of a large family of two component regulatory molecules. Although it has been known for some time that the addition of extraneous sulfate would down regulate the production of several of the virulence factors including PT (Weiss and Hewlett, Ann. Rev. Microbiol. 40:661–686 (1986)), the identification of the compound or compounds that interact with this system remained unknown. In order to determine whether the possible generation of sulfate from cysteine catabolism or another source during the course of *B. Pertussis* growth might affect PT production, a way was sought to either inactivate or remove the influence of sulfate from the culture. Barium in the form of $BaCl_2$ is highly soluble in water (1.8 M at 25° C. and 2.8 M at 100° C.), whereas $BaSO_4$ is highly insoluble (10.7 $\mu$M at 25° C. and 17.7 $\mu$M at 100° C.). This difference in solubility has often been used to precipitate sulfate out of solution for further measurement. Different concentrations of $BaCl_2$ were added to the growth media and the growth and production of PT in the culture were compared. These data are shown in FIG. 5. The addition of the $BaCl_2$ at both concentrations enhanced the production of PT per cell in both *B. Pertussis* strains as compared to the normal media, albeit more in strain 9797. It should also be noted that a visible precipitate could be seen accumulating over time in the culture, presumably $BaSO_4$. These data suggest that the negative feedback inhibitor of PT within the culture is sulfate.

Cloning of a Cysteine Sulfinate Desulfinase gene from BP: One of the possible enzymes responsible for the removal of sulfur from cysteine, nifS-like genes, has been cloned and characterized from *E. coli*. Mihara et al., J. Biol. Chem. 272:22417–22424 (1997). Using this sequence, a homology was sought in the partial *B. Pertussis* genome data base. An open reading frame demonstrating high homology to the nifS genes was found and appropriate PCR primers were synthesized. A PCR product of the appropriate size was generated using *B. Pertussis* chromosomal DNA, was cloned into a TA cloning vector pCR®II-TOPO and was sequenced using methods known to those of ordinary skill in the art (FIG. 7).

Peptide synthesis and purification: A peptide containing the sequence GGGDGSFSGFGDGSFSGFG-OH (SEQ. ID. NO. 5) was synthesized by The Rockefeller University Protein Sequencing Facility using NMP t-butoxycarbonyl chemistry on an ABI 430A peptide synthesizer (Applied Biosystems, Foster City, Calif.). The peptide was deprotected and removed from the resin by treatment with HF in the presence of anisole (0° C./1 h). Preparative purification of the peptide was performed using a C-18 column (2.14 ID×30 cm)(Dynamax-Rainin, Woburn, Mass.). The peptide was quantitated by PTC amino acid analysis using a Waters Picotag system (Waters, Milford, Mass.). The synthesized peptide elute from the C-18 column as a major peak consisting of 95% of the total elution profile. The amino acid composition of the purified peptide was in good agreement with the sequence which was used to synthesize the peptide.

Construction of the peptide affinity column: Superose® 6B was activated using the method described by Brandt, et al., Biochim. Biophys. Acta 386:196–202 (1975). Briefly, a 50% gel slurry of pre-washed Superose® 6B in 0.1 M $NaHPO_4$, pH 8.0, was treated with a solution of 250 mM p-benzoquinone in ethanol to give a final concentration of 20% ethanol and 50 mM p-benzoquinone. The suspension was gently shaken for 1 h at room temperature. The activated Superose® 6B was then extensively washed on a coarse disc sintered glass funnel with 2 volumes each of 20% ethanol, deionized $H_2O$, 1 M NaCl, and once again with deionized $H_2O$. The activated Superose® 6B was aspirated to a compact cake and one volume of a solution containing 2 mg/ml of the peptide in 0.1 M $NaHPO_4$, pH 8.0, was added and the mixture rotated end-over-end for 24 h at 4° C. 1.0 M ethanolamine, pH 8.0, was then added and the rotation continued for 1 h at room temperature. The gel matrix was then wash extensively with deionized $H_2O$, 1.0 M NaCl in 0.1 M $NaHPO_4$, pH 7.0. Aliquots of the initial peptide solution and the supernatant directly after the coupling step were retained and measured by $A_{280}$ using a Shimadzu UV Spec 120 (Shimadzu, Columbia, Md.) to determine the incorporation of the peptide onto the Superose® 6B.

From the foregoing description, one skilled in the art can easily ascertain the essential characteristics of this invention, and without departing from the spirit and scope thereof, can make various changes and modifications of the invention to adapt it to various usages and conditions without undue experimentation. All patents, patent applications and publications cited herein are incorporated by reference in their entirety.

What is claimed is:

1. A method of producing pertussis toxin, comprising cultivating a Bordetella species in a media that comprises one or more salts selected from the group consisting of Ba salts, Sr (II) salts, Pb (II) salts and Ag (II) salts to eliminate or reduce pertussis toxin expression inhibitors; and isolating the pertussis toxin from the media.

2. The method according to claim 1, wherein the salt is a halide salt.

3. The method according to claim 2, wherein the salt is selected from the group consisting of $BaCl_2$ and $BaBr_2$.

4. A method of producing a Bordetella toxin, comprising cultivating a Bordetella species in a media that comprises one or more salts selected from the group consisting of Ba salts, Sr (II) salts, Pb (II) salts and Ag (II) salts, wherein the salts sequester sulfate ions that inhibit expression of the toxin; and isolating the Bordetella toxin from the media.

5. The method according to claim 4, wherein the sulfate ions are byproducts of cysteine metabolism.

* * * * *

SEQUENCE LISTING

```
<160> NUMBER OF SEQ ID NOS: 5

<210> SEQ ID NO 1
<211> LENGTH: 10
<212> TYPE: DNA
<213> ORGANISM: Unknown
<220> FEATURE:
<223> OTHER INFORMATION: recombinant DNA
```

```
<400> SEQUENCE: 1
gattgctgat                                                                10

<210> SEQ ID NO 2
<211> LENGTH: 10
<212> TYPE: DNA
<213> ORGANISM: Unknown
<220> FEATURE:
<223> OTHER INFORMATION: recombinant DNA

<400> SEQUENCE: 2
tagatggggc                                                                10

<210> SEQ ID NO 3
<211> LENGTH: 21
<212> TYPE: DNA
<213> ORGANISM: Bordatella Pertussis

<400> SEQUENCE: 3
atgagcaatc gccccatcta c                                                   21

<210> SEQ ID NO 4
<211> LENGTH: 18
<212> TYPE: DNA
<213> ORGANISM: Bordatella Pertussis

<400> SEQUENCE: 4
cactatttgg tcggtcgg                                                       18

<210> SEQ ID NO 5
<211> LENGTH: 19
<212> TYPE: PRT
<213> ORGANISM: Unknown
<220> FEATURE:
<223> OTHER INFORMATION: synthetic peptide

<400> SEQUENCE: 5

Gly Gly Gly Asp Gly Ser Phe Ser Gly Phe Gly Asp Gly Ser Phe Ser
 1               5                  10                  15

Gly Phe Gly
```